United States Patent
Brewer et al.

(10) Patent No.: US 12,287,333 B2
(45) Date of Patent: Apr. 29, 2025

(54) AUTOMATED SOLID PHASE EXTRACTION USING FILTER TIPS

(71) Applicant: DPX technologies, LLC, Columbia, SC (US)

(72) Inventors: William E. Brewer, Columbia, SC (US); Kaylee R. Mastrianni, Columbia, SC (US)

(73) Assignee: DPX TECHNOLOGIES, INC., Columbia, SC (US)

( * ) Notice: Subject to any disclaimer, the term of this patent is extended or adjusted under 35 U.S.C. 154(b) by 379 days.

(21) Appl. No.: 18/056,150

(22) Filed: Nov. 16, 2022

(65) Prior Publication Data

US 2023/0075131 A1 Mar. 9, 2023

Related U.S. Application Data

(63) Continuation-in-part of application No. 17/403,777, filed on Aug. 16, 2021, now Pat. No. 11,567,067, (Continued)

(51) Int. Cl.
*B01L 3/00* (2006.01)
*B01F 33/302* (2022.01)
*B01F 33/3033* (2022.01)
*B01L 3/02* (2006.01)
*B01L 7/00* (2006.01)
(Continued)

(52) U.S. Cl.
CPC ...... *G01N 33/54366* (2013.01); *B01L 3/0275* (2013.01); *B01L 3/5635* (2013.01); *C07K 1/34* (2013.01); *G01N 1/405* (2013.01); *G01N 1/4077* (2013.01); *B01L 2300/0681* (2013.01); (Continued)

(58) Field of Classification Search
CPC ............ G01N 33/54366; G01N 1/405; G01N 1/4077; G01N 2001/4061; G01N 2001/4088; G01N 35/10; G01N 2035/00524; G01N 2035/103; G01N 2035/1032; G01N 2035/106; B01L 3/0275; B01L 3/5635; B01L 2300/0681; B01L 2200/028; B01L 2200/0631; B01L 2400/0478; B01L 2400/0487; B01L 3/502753; C07K 1/34
See application file for complete search history.

(56) References Cited

U.S. PATENT DOCUMENTS 4,948,561 A  8/1990  Hinckley
6,168,761 B1  1/2001  Kelly
(Continued)

FOREIGN PATENT DOCUMENTS

WO  2012103214 A2  8/2012

OTHER PUBLICATIONS

Rainin. "Pipetting in Forensics" (2014) Mettler-Toledo Anachem Magazine.

*Primary Examiner* — Jennifer Wecker
*Assistant Examiner* — Oyeleye Alexander Alabi
(74) *Attorney, Agent, or Firm* — Boulware & Valoir PLLC

(57) ABSTRACT

Devices and methods for performing pre-analysis sample processing of biological and chemical samples using robotic liquid handlers are disclosed. Methods for solid phase extraction, protein precipitation and filtration of biological and chemical samples using automation and the devices in a rapid and convenient way are described.

9 Claims, 7 Drawing Sheets

Related U.S. Application Data which is a continuation of application No. 16/320,974, filed as application No. PCT/US2017/045024 on Aug. 2, 2017, now Pat. No. 11,193,930.

(60) Provisional application No. 62/462,714, filed on Feb. 23, 2017, provisional application No. 62/369,897, filed on Aug. 2, 2016.

(51) Int. Cl.
| | |
|---|---|
| *B33Y 80/00* | (2015.01) |
| *C07K 1/34* | (2006.01) |
| *C12M 1/00* | (2006.01) |
| *C12M 1/34* | (2006.01) |
| *C12M 3/00* | (2006.01) |
| *C12M 3/06* | (2006.01) |
| *C12Q 1/6848* | (2018.01) |
| *C12Q 1/686* | (2018.01) |
| *G01N 1/40* | (2006.01) |
| *G01N 21/29* | (2006.01) |
| *G01N 33/543* | (2006.01) |

(52) U.S. Cl.
CPC ........... *G01N 2001/4061* (2013.01); *G01N 2001/4088* (2013.01)

(56) References Cited

U.S. PATENT DOCUMENTS

| | | |
|---|---|---|
| 6,171,553 B1 | 1/2001 | Petrek |
| 6,566,145 B2 | 5/2003 | Brewer |
| 6,737,023 B1 | 5/2004 | Kelly |
| 2001/0049092 A1 | 12/2001 | Ekins et al. |
| 2009/0090855 A1 | 4/2009 | Kobold |
| 2010/0081209 A1* | 4/2010 | Brewer ............... B01L 3/0275 436/178 |
| 2011/0020919 A1 | 1/2011 | Fulton |
| 2012/0021526 A1 | 1/2012 | Baer et al. |
| 2012/0252115 A1 | 10/2012 | Suh |
| 2014/0370590 A1* | 12/2014 | Suh ..................... C07H 21/00 435/320.1 |

\* cited by examiner

FIGURE 6 – Prior Art
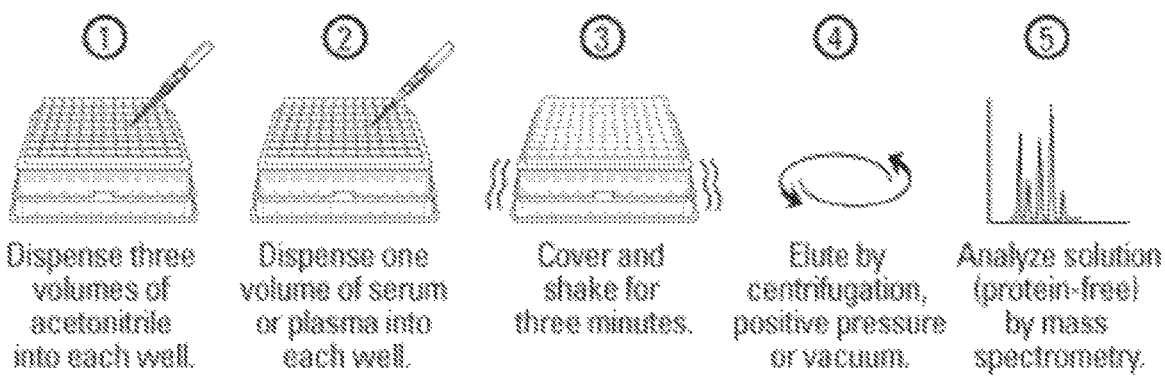
Protein Precipitation Plate protocol summary

AUTOMATED SOLID PHASE EXTRACTION USING FILTER TIPS

PRIOR RELATED APPLICATIONS

This application is a continuation-in-part of U.S. Ser. No. 17/403,777, filed Aug. 16, 2021 (allowed) which is a continuation application claiming priority to Ser. No. 16/320,974, filed Jan. 25, 2019 (U.S. Ser. No. 11/193,930), which is a National Phase filing under 35 U.S.C. § 371 of International Application PCT/US2017/045024, filed on Aug. 2, 2017, which claims priority to U.S. Provisional Application No. 62/369,897, filed Aug. 2, 2016, and U.S. Provisional Application No. 62/462,714, filed Feb. 23, 2017. Each application is incorporated herein by reference in its entirety for all purposes.

FEDERALLY SPONSORED RESEARCH STATEMENT

Not applicable.

REFERENCE TO MICROFICHE APPENDIX

Not applicable.

FIELD OF THE DISCLOSURE

The disclosure relates to devices and methods for solid phase extraction, protein precipitation and filtration of biological and chemical samples using automation.

BACKGROUND OF THE DISCLOSURE

The study of small molecules and their behavior in complex matrices (e.g., serum, plasma, blood, urine, food, soil) is an essential part of pharmaceutical, forensic, environmental and clinical research applications. For instance, researchers develop and run various assays to quantitate drugs, pharmaceutical candidates, and their metabolites in biological fluids, such as serum, plasma and whole blood. The data resulting from these assays are used to help determine the pharmacodynamic and pharmacokinetic properties, as well as the toxic and therapeutic concentrations of existing and emerging pharmaceutical compounds in living cells, tissues, and animals. This evaluation is a critical element of the analytical information utilized during the course of drug development, including the pre-clinical stage, the clinical stage, and the therapeutic drug monitoring stage. Additional, researchers develop and run various assays to quantitate drugs in drug delivery substrates, such as tablets, pills, gels and capsules for quality control and forensic applications.

Unfortunately, most substrates and proteins present in a given matrix interfere with detection of small molecules. For instance, protein content in biofluids can vary from 6% to more than 50% by weight depending on the tissue or fluid sample. This can greatly affect the ability to detect and/or quantify a drug or its metabolite. Thus, the target molecules must be separated and recovered from the protein matrix before analysis.

Protein separation and analyte recovery is accomplished by precipitating proteins with a protein precipitating reagent, typically an organic solvent, vortexing the sample to encourage precipitation, and then separating the supernatant from the protein-precipitate by centrifugation or filtration. The supernatant usually contains the target analytes, which can then be further purified using extraction methods (e.g., solid-phase extraction) or analyzed by standard downstream methods such as LC-MS/MS analysis or radioimmunoassays or spectroscopic techniques. The vortexing and centrifugation method is a time consuming method that usually requires technician involvement.

Many attempts to automate this precipitation and separation process have been made. Protein precipitation plates are becoming common because they increase the throughput, enable fully automated workflows, and improve the overall protein and particulate removal. The protocol for using such plates is shown in FIG. 6. Here, the precipitation reagent and biofluid is dispensed into a well plate (typically a 96-well plate), covered and shaken. The resulting supernatant can then be separated by centrifugation or vacuum or positive pressure manifolds before being analyzed. The need for centrifugation, vacuum or positive pressure manifolds on robotic systems make these systems more complex, more costly, and greatly increase turnaround time for processing samples. In addition, this "in-well" precipitation method suffers from cloudy filtrates and clogged devices. Further, there is an increased risk of sample contamination due to leakage between wells during the shaking step. Additionally, the filtrate may still contain unwanted salts and lipids, especially from human samples. These lipids and salts can be a major contributor to ion suppression and matrix build-up within an analysis system.

Solid phase extraction (SPE) techniques are often employed to separate analytes from other complex matrices found in chemical, food or environmental applications. The SPE procedure is typically performed using a cartridge or plate that contains packed sorbent and incorporates the steps of conditioning the sorbent, loading the target compounds on the sorbent, washing and eluting the targeted compounds.

Other formats for the SPE procedure also exist. For example, immunoaffinity-based extractions using magnetic beads have been developed to enable the required long equilibration times for sorbent/sample interaction. The samples are mixed, at temperature-controlled conditions, with an immunoaffinity resin dispersed in the sample tubes to optimize antigen-antibody interactions. A magnetic field is applied to separate the resin from the solutions and to collect the resin. The magnetic field is also applied during washing and elution steps to separate the matrix from the analyte in the final solution for analysis.

Unfortunately, some disadvantages exist. The use of the magnetic fields increases the complexity of the automation and requires additional accessories for the robot. Also, the resins may not be affected by the applied magnetic fields and end up in the solutions being analyzed. This, in turn, causes problems with the analysis and potential downtime of analytical instrumentation for repair. More importantly, the use of magnetic resins greatly increases the cost of immunoaffinity SPE methods, in addition to the automation requirements.

Solid phase extraction techniques have been automated; however, all of the automated SPE methods utilize additional accessories for robotic liquid handling system. For instance, the liquid solvents and samples are passed through the SPE cartridge using negative pressure with vacuum manifolds, or positive pressure with various positive pressure manifolds; specialized trays for holding SPE cartridges are required; and special adapters are needed to move and manipulate the SPE cartridge. These added accessories increase both the complexity and the cost of the robotic systems.

Further, issues exist with the automation. Automated SPE suffers from an inability to control the flow of the solutions, in particular the loading of the sample solution at which time the targeted compounds (analyte or matrix components) interacts with the sorbent. In the initial step of loading, the targeted compound(s) partition or adsorb to the sorbent. In some cases, a long interaction (or equilibration) time of the targeted compound with the sorbent is needed to achieve high extraction efficiencies, which cannot be reproducibly performed using packed SPE cartridges or plates. Other issues include clogging of the cartridges, irreproducible results due to varying flow rates, and channeling, i.e. where the sample passes through the cartridge without coming in contact with the sorbent.

Thus, there still exists a need for improvements in the automation of chemical and biological samples with complex matrices to decrease sample backlog and remove as many human-dependent steps as possible. Preferably, such improvements do not require additional robotic accessories that increase complexity, which inherently leads to more potential errors and instrument downtime. Further, improvements to the incubation and loading periods that increase the recovery of more analytes are desired. Even minor improvements that reduce the time needed to perform the extraction or protein removal steps without sacrificing the loading of the sample will greatly improve laboratory throughput and success in drug discovery and other applications.

SUMMARY OF THE DISCLOSURE

Disclosed herein are devices and methods of automated filtering of chemical or biological sample preparations that use modified robotic pipette tips for improved separation of matrices and analytes. The automated filtering methods can include steps for solid phase extraction (SPE) and/or protein precipitation. The main advantage for using pipette tips for the device is that they are readily used with automated robotic liquid handlers (RLH). Further, the devices can be implemented on RLH platforms without additional accessories such as positive or negative manifolds that are currently needed with SPE preparations, or a centrifuge and vortex mixer that are needed for protein removal processes, or magnetic fields for immunoaffinity-based SPE.

The device comprises a 'bottom' pipette tip modified with at least a filter and optional substrate, sorbent, or barrier, and a 'top' pipette tip fitted therein for sample and solvent handling. The narrow end of the top pipette tip fits into the bottom pipette tip and forms an air-tight seal. An optional gasket can be used at the contact point between the tips to facilitate the formation of an air-tight seal. This configuration is referred to as a "tip-on-tip" format. This tip-on-tip configuration can be formed by the RLH during automated sample preparations, or manual sample preparations as well, or can be manufactured and sold as a single device in a kit. Methods of using the tip-on-tip device during automation are described.

Because of the unique design of the device, it can be used to perform biological and chemical sample treatments (i.e. extraction, precipitation, filtration, and the like) in a quicker, more efficient automated procedure without additional RLH accessories.

In more detail, the tip-on-tip device includes a bottom pipette tip, also referred to as a "filter pipette tip." The filter pipette tip is a standard or robotic pipette tip fitted with at least one frit or screen and, optionally, a substrate, sorbent, barrier, and/or gasket. The frit or screen is placed at the narrow, distal end of the filter pipette tip to ensure the solutions that pass through the filter pipette tip are free of particulate matter. A 'top' pipette tip is friction fitted or pressure fitted or snap fitted into the bottom pipette tip such that the outer walls of the narrow end of the top pipette tip contacts the inner surface of the bottom pipette tip, or optional gasket, to form an air-tight seal.

The filter in the 'bottom' filter pipette tip can be any screen or frit known in the art such as stainless steel, porous polymeric material, porous glass, porous ceramic, or other similar materials. Preferably, a porous plastic material is used that can be modified to include varying amounts of porosity, where the pores are larger at the top end and smaller at the narrow end to assist with the filtration and prevent clogging. In one embodiment, a series of stacked frits of varying porosities can be used to form the filter. The filter can be positioned at any point in the filter pipette tip. For instance, the filter can be positioned near the proximal (top) end adjacent to the pipette hub to provide the highest surface area to alleviate pressure from clogging. Alternatively, the filter can be located closer to the distal (bottom) end if optional substrates and the like are utilized.

The filter pipette tip can also have additional frits or screens placed in the middle of the filter pipette tip, below the contact point with the top pipette tip and above the original frit or screen at the narrow end. This tip-on-tip configuration provides an easy way to collect and filter sorbent or other solid particulates from a separation process performed in the top pipette tip and separate analytes from sample matrices and other unwanted components.

Because the filter pipette tip is a standard tip, it can be stored in a e.g. 96 pipette tip tray on the RLH platform, without the need for additional accessories or modified trays on the robotic platform.

The top pipette tip can also be a standard tip. However, it is preferably a wide bore pipette tip for biological or viscous samples. Wide bore pipette tips are simply tips that have a larger orifice at the distal, narrow end than traditional standard or robotic pipette tips. The orifice can be much larger than traditional pipette tips. A standard or robotic pipette tip can be modified to a wide bore tip by cutting a couple of millimeters or even centimeters off of the narrow end of the tip. The hub (proximal end that attaches to the pipettor) is still wider in diameter than the modified narrow end.

In some embodiments, the top pipette tip is friction or pressure fitted directly to the filter pipette tip using the RLH to form a single piece tip-on-tip device. This means that the outer walls of the narrow end of the top pipette tip contacts the inner walls of the filter pipette tip.

Applicant has found that the force required to seat the pipette tips directly may not be achievable for certain RLHs or, if achievable, may result in damage to the RLH over time. To accommodate such issues, a gasket can be placed at the contact point of the two pipette tips.

For instance, the top pipette tip can have a gasket on its outer surface that forms an air-tight seal with the inner walls of the wide end of the filter pipette tip during the pressure fitting stage. This contact point can even be as high as the hub of the filter pipette tip. Or, a gasket is placed inside the wide opening end (hub) of the bottom filter pipette tip, opposite the frit or screen to facilitate the air-tight seal with the top pipette tip. Applicants have found that placing the gasket at or below the hub of the bottom filter pipette does not interfere with the RLH's ability to pick up and move the bottom filter tip. Both embodiments using a gasket will require a minimal amount of force from the RLH.

In practice, the RLH inserts the top pipette tip into the bottom pipette tip, and the gasket seals the two pipette tips. Such an arrangement requires less force from the RLH without sacrificing the air-tight seal. Further, depending on the type of gasket, the seal can be reversible, allowing the RLH to pick up and move the top pipette tip at a later point in the process.

When the gasket is on the top pipette tip, its placement should be towards the upper, wider end of the top pipette tip to avoid contact between the gasket and samples and solvents being aspirated. Further, accommodations for this gasket on the pipette tip trays will need to be considered. Ideally, the gasket will be located below and adjacent to the hub of the top pipette tip. This will prevent the gasket from coming in contact with anything other than the inner surface of the filter pipette tip but will allow the top pipette tip to be stored in standard pipette tip trays on the RLH without adding too much height or affecting the clearance between the RLH arm and pipette tips in the pipette tip tray.

The gasket for insertion in the filter pipette tip can be any gasket known in the art but is preferably a thermoplastic or rubber o-ring, and most preferably a square or rectangular thermoplastic o-ring. Square and rectangular o-rings have multiple contact points with both the filter pipette tip and the top pipette tip allowing the tips to be snuggly attached with little 'push back' from the o-ring. Other shapes of o-rings are also possible options for the gasket, but may exert more 'push back' on the top pipette tip and reduce the air-tight seal.

The gaskets need not be separable from the tip, but can be integral therewith. For example, gasket material, e.g. a soft polymeric material, can be painted thereon, or dip coated thereon, and the like. Alternatively, U.S. Pat. Nos. 6,737,023, 6,168,761 and 6,171,553, each incorporated by reference herein in its entirety for all purposes, describes a "soft tip" pipette tip, and these principles could also be used to provide an air-tight seal with low force.

The gasket may consist of two or more square or rectangular o-rings. The placement of the gasket inside the filter tip is preferably on the inner surface, below the hub where the pipette head would make contact; this ensures the filter pipette tip can still be accessed by the RLH. If the gasket is placed at the hub position, the filter tips can only be used for the tip-on-tip procedure (i.e., only makes a seal with another pipette tip). While this may not be an issue in sample preparation techniques when the final step is filtration through the tip, it still limits the applicability of the device.

Alternatively, the gasket comprising thermoplastic, rubber, silicone, soft plastic material, and/or shrinkable plastic material can be placed on the exterior of the top pipette tip. A shrinkable tubing, for example, can be attached to the top pipette tip, just below and adjacent to the hub, and shrunk into place. Shrinkable plastic is typically nylon or polyolefin. However, any plastic that is capable of shrinking radially (but not longitudinally) when heated is preferred. Additionally, the shrinkable plastic can have a thermoplastic adhesive on its inner surface to provide better adhesion to the top pipette tip. Heat shrink tubing, however, may make the size of the gaskets irreproducible from tip to tip, so using specifically sized gaskets may be preferable to ensure the robust process of using high throughput RLH systems.

Regardless of whether the gasket is placed on the outer surface of the top pipette tip or the inner surface of the filter pipette tip, it must be located such that both pipette tips are preferably accessible by a pipettor (either handheld or on a RLH) and the top pipette is not piercing the screen or frit in the filter pipette tip.

In some embodiments, only the filter tip is manufactured and sold, as the top pipette tip can be a standard pipette tip. In yet other embodiments, the top and bottom pipette tips are sold as a kit, allowing the user to make the tip-on-tip device by hand or with the RLH system during sample processing.

In any of the above devices, the top pipette tip is used to mix the sample solution with solvents and/or optional sorbents, and subsequently aspirates the sample solution (with or without the sorbent) and dispenses into the filter pipette tip for filtering. The top pipette tip is able to readily dispense the sample solution through the filter pipette tip because of the air-tight seal.

The filter pipette tip can also include optional substrate, sorbent, or barriers in addition to the screens, frits, and gasket. The substrate or sorbent can be contained between two porous frits or screens. Both the top and bottom filters can be composed of the same or different materials and can have the same or different characteristics such as pore size, number of frits and the like. The top most barrier or screen is below the contact point between the top and bottom pipette tip of the tip-on-tip device. Further, the top pipette tip does not contact or, preferably, pierce the bottom most barrier, screen or frit in the bottom pipette tip.

In other embodiments, the optional substrate in the filter pipette tip is held in place between the bottom filter and a pierceable barrier (for the wide bore pipette tip to pierce) or removable barrier, located at the top end of the filter pipette tip above or below the gasket. It is well known to use conventional pipette tips to puncture sealed containers to access the specimens or samples contained therein. In this method, the sealed container is the filter pipette tip and the wide bore "top" tip is used to pierce the barrier.

The pierceable barrier can be any known in the art including pierceable foil, film, membranes or tape. In some embodiments, the material may be silicone rubber, soft rubber, neoprene, other suitable pierceable material(s), or a combination thereof. The pierceable barrier also acts to contain the substrate within the filter pipette tip during storage and transportation. In other embodiments, the barrier is removable such that a user can remove each barrier as needed or can remove the barrier for a 96-piece tray of filter pipette tips at once.

The positioning of the barrier in the filter pipette tip will depend on the desired conditions of tip-on-tip contact. In some embodiments, the barrier will be positioned towards the proximal end (near the hub, but below the optional gasket) of the filter pipette tip to prevent any physical contact between the wide bore pipette tip and the bottom (i.e. narrow end) of the filter pipette tip. In other embodiments, the barrier may be closer to the screen or frit. This lower barrier can act as part of the filtration step, but also allow the filter pipette tip to contain additional substrate or sorbent that may be used to remove matrix components. In yet other embodiments, the barrier is positioned to prevent contact between the top wide bore pipette tip and any substrate within the filter pipette tip.

The optional substrate in the 'bottom' filter pipette tip can comprise a substrate that has minimal active sites so that the target compounds (matrix components or analytes) can stick to the substrate. The substrate helps with cleaning and filtering the solution and preventing blockage of the filter inside the tip. Exemplary substrates include resin, glass wool, fibrous material, silica, modified silica (such as C4, C8 or C18), fibrous silica, polymeric sorbent, ionic polymeric sorbents, or combinations thereof. The sorbent may also contain material designed to remove phospholipids or other specific matrix components.

The substrate can have absorbent properties to bind specific compounds. Sorbents are a type of substrate that can be chosen to selectively bind compounds. Excessive background from endogenous matrix components is a great concern in bioanalysis. In bioanalytical mass spectrometry, the issue of excessive background contributes to the growing problem of ion-suppression. Ion-suppression is caused by one or more interfering components or species that co-elute with analyte(s) of interest during LC-MS analysis and manifests itself as a loss of analyte response. This results in poor assay reproducibility, accuracy, and sensitivity, especially at the lower limits of quantitation (LLOQ). The sorbent may be used to bind these matrix compounds that cause ion suppression. The sorbent can also be used to bind sample matrices that may irreversibly bind to analytical columns used in LC- or gas chromatography (GC)-MS systems.

Many sorbents are known in the art and can be utilized in the filter pipette tip. Sorbents can utilize Lewis acid/base interactions to bind unwanted compounds or ion exchange mechanisms (i.e. cation or anion exchange mechanisms or non-polar interactions). Ideally, the sorbent is silica or polymeric-based with the desired functional groups attached therein. For instance, the sorbent can be an anion-exchange material with functional groups comprising primary amines, secondary amines, tertiary amines, heterocyclic organic compounds containing nitrogen atom or a combination thereof. Materials having sulfonic groups can be used for cation-exchange. Other functional groups can include acidified metal oxides, lanthanides, and the like. In some embodiments, the sorbent is a weak anion exchange resin. The binding may be accomplished with the need to add additional acid or bases to the sample.

The substrate may also be a sorbent that targets biological sample matrix components, or may be the same type of sorbent as that used in the HPLC column phase. In some embodiments, a combination of sorbents is utilized to bind a combination of matrix components but not analytes of interest.

The most common and problematic biological matrix components are phospholipids, which are present in blood at about 1 mg/mL level. For phospholipids, the sorbent typically has a Lewis acid (i.e. electron acceptor) to interact and bind with the phosphate group on the phospholipids. Examples of such sorbents include the Hybrid™ sorbent by Sigma-Aldrich; the Phree™ sorbent by Phenomenex; Isolute PLD from BioTage; Captiva sorbent from Agilent Technologies; and Ostro™ sorbent from Waters. At least one sorbent in the bottom filter pipette tip can be selected to bind phospholipids.

A common biological matrix issue with urine samples is the conjugation of the analyte with glucuronic acid. Urine samples undergo an acid- or enzyme hydrolysis procedure to deconjugate the analyte(s) before the samples can be analyzed downstream. The sorbent in the filter pipette tip can be chosen to remove the enzyme (beta-glucuronidase or sulfatase) used in the hydrolysis step. For instance, a filter pipette tip containing C4, C8 or C18 sorbent, or silica or fibrous silica, will be able to remove protein and the enzyme used for hydrolysis from the urine sample during the filtration method using a completely automated process. Another possible sorbent may be immunoaffinity-based to selectively bind the enzyme. Phenomenex (Torrance, CA) also has a sorbent called B-gone that removes β-glucuronidase enzyme.

The optional sorbent in the filter pipette tip can also be selected to match the sorbent used in an HPLC column's stationary phase, thus allowing the tip-on-tip device to act as a "guard cartridge". HPLC instrumentation experience increasing pressures from repeated injections of complex samples such as blood, tissue homogenate or even food due to the injection of compounds that bind, in some cases irreversibly, to the stationary phase of the HPLC column. To address this problem, HPLC instrumentation is often fitted with 'guard columns' that are essentially miniaturized HPLC columns with filters. In theory, the problematic compounds bind to the stationary phase in the guard column instead of the HPLC column. As guard columns are less expensive than the HPLC column, they can be replaced periodically, for example, after every 200 injections, to protect the HPLC column and expand its lifetime of use. However, the replacement of the guard column still causes downtime for the LC/MS analysis. Further, the replacement of the guard column may actually cause shifts in retention times of target analytes.

Thus, if the optional sorbent in the bottom filter pipette tip matches the HPLC column's stationary phase, the tip-on-tip device can act as a 'guard cartridge' in place of the guard column. When a sample is processed using this method, the resulting solution would be free from proteins, particulate matter and any compounds that would bind to the HPLC stationary phase.

The optional sorbent can also be selected to bind analytes of interest. Such sorbent would undergo the typical "bind-wash-elute" sequence. After the initial binding step, the wash solvents can be used to clean the analyte-bound sorbent and elution solvents can be used to unbind the analytes, thus allowing its analysis.

The optional sorbent in the bottom filter pipette tip can be different than sorbents used in the extraction or precipitation processes performed by the top pipette tip.

In use, the top pipette tip gathers samples, solvents, buffers, sorbents and the like and performs one or more sample preparation steps such as repeated aspiration and dispensing of the e.g. sample, solvents, buffers, sorbents. The RLH then aspirates the sample (or a portion of the sample) one final time and moves the 'loaded' top pipette top to a 'bottom' pipette tip modified with at least a filter. The force exerted by the RLH is able to seat the top pipette tip into the bottom pipette tip to create an air-tight seal. This seal allows the top pipette tip to elute its contents into the bottom pipette tip, through the filter, and subsequently into a sample vial. The bottom pipette tip acts as a filter such that the solutions pass through this tip free of particulate matter.

It is imperative to mention that filtration (or the dispersive SPE methods described below) can be used with filter plates rather than filter pipette tips. For example, a sample with particulate matter (or sorbent from dispersive SPE, after mixing with the sample solution and being loaded with the analyte(s)) can be collected and transferred to the filter plates instead of using the bottom filter pipette tip in the tip-on-tip device. However, a major advantage of using tip-on-tip device is that the tips allow for random access, hence an entire plate of 96 samples does not have to be used if wanting to analyze less than 96 samples. Further, the cost of having positive/negative pressure manifolds for use with the filter plate is circumvented. The lack of these manifolds reduces the complexity of the process, which greatly reduces incidences of errors, and clears up deck space and/or reduces the overall footprint of the RLH platform. Additionally, during comparison experiments, the Applicant found the tip-on-tip methods to be much faster because it lacks the additional steps required to engage the filter plate and manifold accessories. Thus, not only does the tip-on-tip device reduce the need and cost associated with additional accessories for the RLH, it also reduces preparation time, which will result in higher throughput of samples.

The tip-on-tip device can be used for many sample preparations techniques performed on biological and chemical samples, ranging from simple filtration or cleanup methods for liquid samples (typically environmental, food, pharmaceutical, and the like samples) to protein precipitation of blood (including plasma and serum) and urine samples.

For simple filtration, a sample solution is aspirated into the top pipette tip, then the tip-on-tip device can be created by pressing the top pipette tip (still loaded with sample) into the filter tip to form an air-tight seal before dispensing the sample through the tip-on-tip device into a sample well. Additional steps can be added to the front end or the back end of this simple filtration process to clean, extract, or prepare more complex samples and target compounds for analysis.

Methods of using the tip-on-tip device are exemplified below with respect to common biological and chemical sample preparations. However, this is exemplary only, and the invention can be broadly applied to any sample preparation methods that are commonly employed by RLHs. This summary is provided to introduce a selection of concepts that are further described below in the detailed description. It is not intended to identify key or essential features of the claimed subject matter, nor is it intended to be used as an aid in limiting the scope of the claimed subject matter.

Method 1: Protein precipitation performed separately using a 'top' wide bore pipette tip followed by filtration using the tip-on-tip device. The 'bottom' filter pipette tip can have optional substrates, sorbents, barriers, or gaskets.

Applicant has found that it is possible to perform protein precipitation using a dispersive pipette extraction (DPX) tip without the need for another top pipette tip. The serum or plasma can be aspirated directly into the DPX tip, then followed by aspiration of organic solvent such as acetonitrile to precipitate the proteins. Repeated aspiration and dispensing of the solution results in a sample solution that is free from protein and ready for analysis. However, Applicant's research has shown this method provides inaccurate results for analyzing vitamin D metabolites in serum; and, it is still possible that particulate matter can still be present in the final solution.

With the current tip-on-tip method, the extractions are much more reproducible and accurate, and there are no concerns of particulate matter in the final solutions for analysis due to the filtration. This method is a much improved method for addressing the issues presented by the single DPX tip.

Method 2: Dispersive SPE performed using the top pipette tip followed by filtration with the tip-on-tip device. The top pipette tip is used to transfer sample solution that contains solid particulate matter. The solid particulate matter may be inherent to the sample, or from a dispersive sorbent SPE step performed in the top pipette tip, or may be created due to protein precipitation and/or other treatment of the sample solution. The bottom filter pipette tip filters the solid particulate matter such that a 'clean' liquid passes through. Additional steps such as wash and elution can be performed on the particulate in the tip-on-tip device.

This method can be applied to 'cleanup' solid phase extraction, where the sample solution is first mixed with sorbent using the top pipette tip to bind and remove sample matrix components from the solution; the filter pipette tip is subsequently used to collect the sorbent and allow for analyte-rich solution to pass through for further analysis. Similarly, immunoaffinity resin sorbent can be used to bind and remove proteins in serum or plasma samples before the filtering step.

This method can also be used for binding analytes using the dispersive sorbent before a traditional bind-wash-elute process. Here, the sample solution is first mixed with sorbent in the top pipette tip to bind or partition analytes from the sample solution; the filter pipette tip is used to collect the sorbent that contains the analyte of interest, and the filter pipette tip is then subsequently treated with wash and elution solvents to obtain solution rich in analyte and free from most sample matrix interferences. The collected sorbent may be used for conventional SPE methods, or can also be immunoaffinity resin in which the antibodies are targeting the analytes of interest which are enriched and purified using elution solvent.

It should be mentioned that in some cases, it may be preferable to add wash and elution solvents to the top of the pipette tip containing the sorbent. In particular, highly nonpolar compounds may interact with the filter and sorbent such that addition of solvents from the bottom of the tip do not efficiently remove these compounds. Moving the solvent in one direction from the top to bottom of the tip will provide higher recoveries. In this case, the sealing of the tip-on-tip may require a "reversible" seal, one that allows the top pipette tip to seal and unseal the bottom tip. In a reversible format, the bottom tip would have to be contained in some kind of rack where the top tip makes a seal by "pressing" down on the filter tip to provide the seal. Simply lifting the top tip up from the bottom filter tip, the seal is broken, using only low forces such as can be easily produced by a robotic arm without wear and tear on the mechanics of the robotics. Then solvents can be readily added to the top of the filter tips.

Method 3: The precipitation or binding of target compounds to a sorbent is performed using the tip-on-tip device. The 'bottom' filter pipette tip must have sorbent and/or optional barriers. In this method, the sample is added to the top of the bottom filter tip containing the sorbent using the top pipette tip. The top tip seals the bottom filter tip, the sample is delivered to the sorbent of the bottom filter tip, and then the tip-on-tip device aspirates the precipitation reagent to "crash" the proteins of the sample solution. The difference between method 1 and method 3 is that the sorbent is used to assist with the protein precipitation and subsequent analysis.

In some embodiments, where the sample is viscous (such as with saliva or tissue homogenates), the sample may be too viscous to easily and completely enter the sorbet slurry. In such cases, the sample and/or the sorbent slurry may be diluted with solvent or buffer, and absorption steps may also be repeated.

In any of the above methods and embodiments, the 'bottom' filter pipette tip is a standard or robotic pipette tip fitted with a frit or screen and, optionally, a substrate, sorbent, or barrier. The top pipette tip fits within the filter pipette tip to form an air-tight seal and create a tip-on-tip format. Some RLHs may not be able to exert enough force to seal the tip-on-tip device. Thus, some embodiments include gaskets, such as a square o-ring or shrinkable tubing or rubber gasket, on one of the pipette tips that allows the two tips to be seated to form an air-tight seal and alleviates the force needed from the RLH. This allows the tip-on-tip device to be created and used by RLHs from any manufacturer.

A good pipette tip with good fit to the pipettor or RLH should be expellable with less than 0.5 kg (5 Newtons) of force. There are many, however, that require additional force (e.g., upwards of 80 kg), but these indicate a less than ideal fit (e.g., a universal tip), and will wear on human or mechanical machinery with thousands of repeat actions. Thus, it is preferred that the tips function at about 1-20 N of force, 0.5-10 N or ideally about 5 N. Thus, the fit to each other and to the RLH plus the gasket should function within this range.

Once the air-tight seal is established, the solution in the top pipette tip can be dispensed from the top pipette tip through the filter pipette tip, and optional substrate, which cleans and filters the solution. The clean sample solution can then undergo additional SPE and/or direct analysis by downstream analytical methods.

For protein precipitation applications, any biological sample can undergo protein precipitation using the device and methods. Any precipitation reagent known in the art for protein precipitation can be used. Organic solvents such as acetonitrile, propionitrile, tetrahydrofuran (THF), methanol, ethyl acetate, hexane, isopropanol, ethanol, ethanol-petroleum ether, dioxane, dimethylsulfoxide, dimethylformamide, acetone, heat, acid, phenol, and methylene chloride are commonly used. Trichloroacetic acid, zinc sulfate and urea can also be used to initiate protein precipitation. The liquid solutions can be added to the wells directly from solvent reservoirs using the robotics, or the wells could already contain solid substrates if needed or preferred. Most preferably, acetonitrile or methanol is used for serum, plasma or whole blood applications.

Because biological samples tend to be viscous and/or have solid matter therein, the top pipette tip is preferably a wide bore pipette tip to allow for easy aspiration and dispensation, which leads to better interaction between the sample and reagents.

Once the protein precipitate has been removed, the cleaned sample can undergo analysis or further sample preparation. For instance, solid phase extraction methods can be used to extract out certain target molecules such as free drugs, nanoparticles used for drug delivery, and/or drug-antibody conjugates.

Ideally, the additional sample preparations are also automated to maintain chain-of-custody through limited human interaction. For instance, some solid phase extraction devices, such as dispersive pipette extraction (DPX) tips, have been adapted for automation. Thus, the protein precipitation, extraction and analysis are all automated to decrease analysis time, increase throughput, and limit human intervention.

Or, as mentioned above, immunoaffinity resin sorbent can be used to bind and remove proteins of high abundance in serum or plasma samples.

Ideally, the entire sample preparation process is automated by the RLH. Automation of the protein precipitation or matrix removal replaces the complexities of vortex mixing and centrifugation with automation and removes the human element. Further, the additional sample preparations are also automated to maintain chain-of-custody through limited human interaction. Thus, the protein precipitation, extraction and analysis are all automated to decrease analysis time, increase throughput, and limit human intervention. Additionally, by not utilizing centrifugation, vacuum or positive pressure manifolds during the filtration process, basic and less expensive robotic systems can be used with the methods.

Any analytical method can be paired with the automated sample preparation methods including liquid or gas chromatography coupled with mass spectrometry, radioimmunoassays and nonisotopic assays such as fluorescence polarization immunoassays or enzyme linked immunosorbent assays.

Again, this summary of the methods using the tip-on-tip device is provided to introduce a selection of concepts and is not intended to identify key or essential features of the claimed subject matter, nor is it intended to be used as an aid in limiting the scope of the claimed subject matter.

Further, while the devices and methods are suited for automation, it is also possible to implement the devices and the described methods by hand. In such situations, the aspirating and dispensing will be performed using a plunger attached to the top pipette tip, or the bottom filter pipette tip. Such modifications to perform the methods by hand are well within the purview of one with ordinary skill in the art.

The methods are described with reference to biological matrices obtained from humans. However, it should be understood that such methods can utilize biological matrices from animals, as well as environmental samples, food samples, pharmaceutical samples and the like.

The term "pipette tip" is a term of art, and refers to a conical tube with a larger end, called the "hub" herein, and a narrow end, called the "delivery tip" herein, which is precisely engineered for accurate sampling and delivery of fluids. The hub fits over the barrel of the pipette or robotic liquid handler, typically by friction fit. The interior diameter of the tip hub must be slightly larger than the barrel of the pipettor and the inside taper of the tip must also match the taper of the pipette barrel. Most manufacturers of hand held pipettors and robotic liquid handler systems make pipettors that will utilize universal tips. The hub is located at the proximal end of the pipette tip and the delivery tip is located at the distal end.

The pipette tip fits onto the barrel of the micropipettes in an air-tight manner, such that when the plunger of the pipette is pressed and released, a vacuum is applied, and fluid is pulled into the pipette tip. That fluid can be delivered to any receptacle as needed by again depressing the plunger. Some pipette tips are sealed to the barrel of the pipettes through the use of gaskets rather than the taper of the pipette tip. Some robotic pipette tips are not friction fitted, but use an expandable o-ring to make the air tight seal required for liquid pipetting. As such, pipette tips are available in a range of sizes to fit different pipettes.

Preferably, the pipette tip has one or more ridges on an outer surface near the hub, such that the ridge(s) allow the tip to be stored on a platform having an array of holes, the ridges preventing the conical tip for sinking too far into the hole and risk getting stuck. Such ridges are common on pipette tips. Common ridge styles include an annular ridge that completely circumnavigates the pipette tip, and a plurality of vertical fins, which provide strength, support the tip on the hole, and also minimize materials and weight. Combinations are also common. In some embodiments, the ridges are used to store the pipette tip on the neck of the housing.

The term "robotic pipette tip" is a pipette tip whose inner taper in the hub is such as to fit a robotic liquid handler. Most frequently there is no difference between a robotic pipette tip and a pipette tip for a hand-held pipettor, but there can be size differences.

A "wide bore pipette tip" is a pipette tip whose delivery tip has a wider orifice than standard traditional or robotic pipette tips of similar volume size. Typically, the distal end orifice is much larger than the standard tips. The wide bore pipette tip can have a hub capable of fitting a standard pipettor or robotic liquid handler.

The term "filter pipette tip" refers to a pipette tip, either standard or robotic, that has been modified to have a filter, screen, or frit located at the distal (bottom) end near the narrow opening. The filter pipette tip can optionally include a substrate, a sorbent, a barrier, or a combination thereof, and optionally a gasket.

The term "tip-on-tip" refers to the configuration of a 'top' pipette tip fitted inside a second 'bottom' pipette tip. The top pipette tip is typically a standard or wide bore pipette tip and the bottom pipette tip is the filter pipette tip, with optional substrate, sorbent, barrier, or a combination thereof. The top pipette tip does not have to be wide bore, but wide bore allows for mixing of sample solutions that contain solid particulate matter and/or are viscous.

The term "substantially free" means having no more than 50% of the original protein or other contaminant concentration, preferably less than 10% and, most preferably less than 5% of the original contaminant concentration.

A "robotic liquid handler" is a robotic system, used for automation in chemical or biochemical laboratories that dispenses a selected quantity of reagent, samples or other liquid to a designated container. The simplest version can dispense an allotted volume of liquid from a motorized pipettor or syringe; more complicated systems can also manipulate the position of the dispensers and containers (often a Cartesian coordinate robot) and/or integrate additional laboratory devices or add-ons, such as microplate readers, heat sealers, heater/shakers, bar code readers, spectrophotometric or separation devices and instruments, storage devices, waste containers and incubators. In addition to the motorized pipettor or syringe, robotic liquid handlers also have trays for sample wells or trays for holding sample vials, trays of pipette tips that fit the pipettor, and containers of solvents. The biological samples in the present invention can be in sample wells, vials, or any other sample container used on RHLs currently or developed in the future.

The methods described herein require a robotic liquid handler capable of manipulating the position of pipette tips on the Cartesian, 3-axis movements, typically implemented by means of an arm, and having multi-pipetting capabilities. To further reduce human interaction, it is also desirable to have spectrophotometric or separation instruments integrated with the handler.

Exemplary robotic liquid handlers include the Star or Starlet or Nimbus from Hamilton Company; Bravo Automated Liquid Handling Platform from Agilent; the epMotion from Eppendorf; the Biomek 4000 or NX or FX from Beckman Coulter; the PIPETMAN from Gilson; the Freedom Evo from Tecan; and PAL systems from CTC or the MPS from GERSTEL, which are capable of being modified to perform pipetting and integrated with a variety of separation-mass spectrometric instruments. However, any commercially available robotic liquid handler can be used and/or modified to perform the disclosed precipitations.

The term "precipitation reagent" refers to a reagent or solvent used to precipitate proteins, hemoglobin and the like out of biological samples such as serum, plasma, whole blood, urine, spinal fluid, meconium and tissue homogenate.

"Guard columns" are small HPLC columns installed in front of an analytical column, in order to protect it from strongly retained impurities, thus prolonging the life of the analytical column.

"Guard cartridges" are devices that have sorbent positioned between two filters. The sorbent preferably matches the liquid chromatography column phase such that biological matrix components will bind to the sorbent in the cartridge before the sample is introduced to the HPLC. This protects, or guards, the LC column and thus expands its lifetime of use. Unlike the guard columns, the cartridge does not have to be installed on the HPLC instrumentation.

As used herein, the term "membrane" refers to a thin pliable film that acts as a barrier. In this application, the membrane will protect and contain the substrates and sorbents within the filter pipette tip during storage and transport. The membrane can be placed on the filter pipette tip during manufacturing using means known in the art.

As used herein, the term 'cleanup' solid phase extraction denotes sorbent that binds or partitions sample matrix components, but does not interact with analytes of interest.

As used herein, the term "bind-wash-elute" refers to a process commonly employed with solid phase extraction. The sorbent binds or partitions analytes of interest; then wash solvents are used to remove other contaminants from the sorbent, before an elution solvent is used to remove the bound analytes from the sorbent for analysis.

As used herein, the term "gasket" refers to a shaped piece of soft material used for sealing the junction between two surfaces. The gasket fills the space between two or more mating surfaces. Gaskets are normally made from rubber, silicone, metal, cork, neoprene, nitrile rubber, fiberglass, polytetrafluoroethylene (otherwise known as PTFE or Teflon), a plastic polymer (such as polychlorotrifluoroethylene) and other material that has some degree of yielding to allow for the deformation needed to fill the space between the two surfaces. As noted, the gasket can be integral with the pipette piece or a removable piece added thereto.

As used herein, the term "target compounds" refers to the compounds that the sorbent(s) will bind. The term can refer to either analytes of interest or unwanted components, but never both at the same time because the purpose of most sample preparation techniques is to separate the analytes of interest from unwanted components.

As used herein, the term "dispersive" refers to the solid phase sorbent or substrate being loosely contained, allowing it to be thoroughly mixed with liquid solutions aspirated into the pipette tip. Normally, solid phase sorbents are packed into cartridge to eliminate movement of the sorbent. The present methods utilize the dispersive nature of the loose sorbent to improve mixing and interaction with the target compounds.

As used herein, "air-tight" is used to describe the seal between the inner surface of the bottom pipette tip and the outer surface of the top pipette tip and simply means that no gases (e.g. air) passes at this point of contact. The flow of gas is relegated to the opening of the pipette tips at operating pressures.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| DPX | Dispersive pipette extraction |
| HPLC | High Performance Liquid Chromatography |
| LC/MS/MS | Liquid Chromatography/Mass spectrometry/Mass spectrometry |
| MS | Mass spectrometry |
| RLH | Robotic Liquid Handler |
| RT | Retention time |
| SPE | Solid phase extraction |
| WAX | Weak anion exchange |
| GC-MS | Gas chromatograph mass spectrometry |
| RSD | Relative standard deviation |
| API | Active pharmaceutical ingredients |

BRIEF DESCRIPTION OF THE DRAWINGS

FIG. 6. Prior Art. Protein Precipitation Plate Protocol obtained from ThermoFisher Scientific.

DESCRIPTION OF EMBODIMENTS OF THE DISCLOSURE

Figure 1:
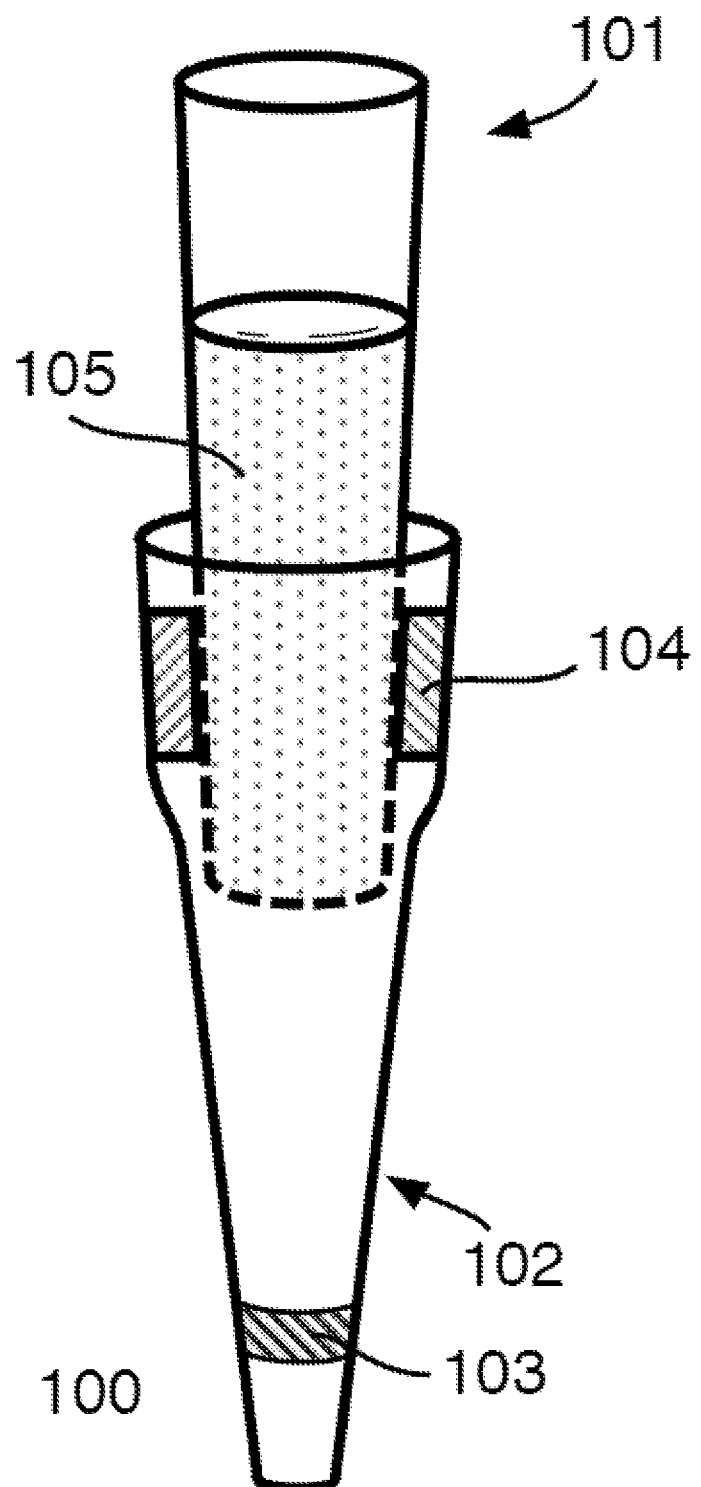
FIG. 1. Tip-on-tip device with optional gasket on the bottom filter pipette tip.

The invention provides novel devices and methods for automating cleaning, extraction, and/or filtration of biological or chemical samples using robotic liquid handlers without centrifugation or positive pressure manifolds or time-consuming vortex and centrifugation steps.

The present devices and methods were developed to overcome the complexities and time commitment of vortex mixing and centrifugation of biological samples. Through the use of automated robotic liquid handlers (RLH), a user is able to dispense a sample into a sample vial on the RLH and allow the RLH to perform protein precipitation and subsequent analysis with little to no intervention by the user. This method decreases the time needed for precipitation and collection of supernatant, leading to higher throughput, while minimizes the user's time and sample interaction. Moreover, this method eliminates the need for more expensive accessories to robotics such as centrifuges, vortex mixers, vacuum and/or positive pressure manifolds.

The methods described herein use a unique pipette tip-on-tip format wherein a top pipette tip performs the mixing for the protein precipitation before eluting the solution through a bottom pipette tip that has been modified to include a screen or frit, which filters and cleans the solution. Optional substrates can be used in the bottom pipette tip to improve filtering. Additionally, the bottom pipette tip can utilize a barrier to contain the substrate and keep it 'fresh' until needed. This barrier can be pierceable by the top pipette tip, or can be removed by the user prior to use. Or, the barrier can be positioned low in the bottom pipette tip and used as part of the filtration step.

Due to the size and volume of the proteins being precipitated, the top pipette tip is a large or wide bore pipette tip, meaning it has a larger orifice in the distal end than the typical pipette tip or robotic pipette tip. Such pipette tips are commercially available, although standard pipette tips can be modified in-house by removing the bottom 2-20 millimeters of the distal, narrow end of the standard pipette tip. The wide bore pipette tip's mixing of the sample and solvents is comparable to vortex mixing.

Alternatively, the top pipette tip can elute a biological sample onto a sorbent contained in the bottom, filter pipette tip. Then, both pipette tips in the tip-on-tip device performs the mixing for the precipitation by repeatedly aspirating and dispensing the precipitation reagent through the sample-entrained sorbent.

In developing these methods for protein precipitation, other applications to chemical samples were also realized due to the improved mixing experienced with the wide bore tip. This includes an initial analyte-loading step on sorbents, similar to the protein precipitation using the top pipette tip, followed by filtration and separation of the sorbent from the sample matrices. Additional steps to elute the analyte(s) from the sorbent follow. The reverse, with loading of the sample matrices and contaminants onto the sorbent and removal of them and the sorbent from the 'clean' analyte filtrate is also possible.

One embodiment of the disclosed tip-on-tip device 100 is shown in FIG. 1. It comprises a top pipette tip 101 for collecting samples or solvents, and for mixing samples with other additives such as precipitation reagents or sorbents for dispersive extraction. The bottom pipette tip 102 is, in its most basic form, used to filter solid particulates from samples using a filter, frit or screen 103. The bottom pipette tip 102 can also include a gasket 104 for facilitating an air-tight seal between the tips. In use, a robotic liquid handler (RLH) carries the top pipette tip 101, usually with a sample solution and/or sorbent 105 to the bottom pipette tip. It seats the top pipette tip 101 in the bottom pipette 102 to form an air-tight seal. As some RLH do not generate enough force to create this seal using just the pipette tips, a gasket 104 can be used to minimize the force required of the RLH to insert and seal the "Tip-On-Tip" device. Further, the gasket (as an o-ring) may offer a reversible seal between the pipette tips. However, the gasket is optional.

In its most basic embodiment, the bottom pipette tip 102 is used as a filtering device. The frit 103 prevents solids from passing through the tip. This allows the solution that collects in the vial below the tip-on-tip device 100 to be contaminant and solid free and ready for analysis.

Figure 2A:
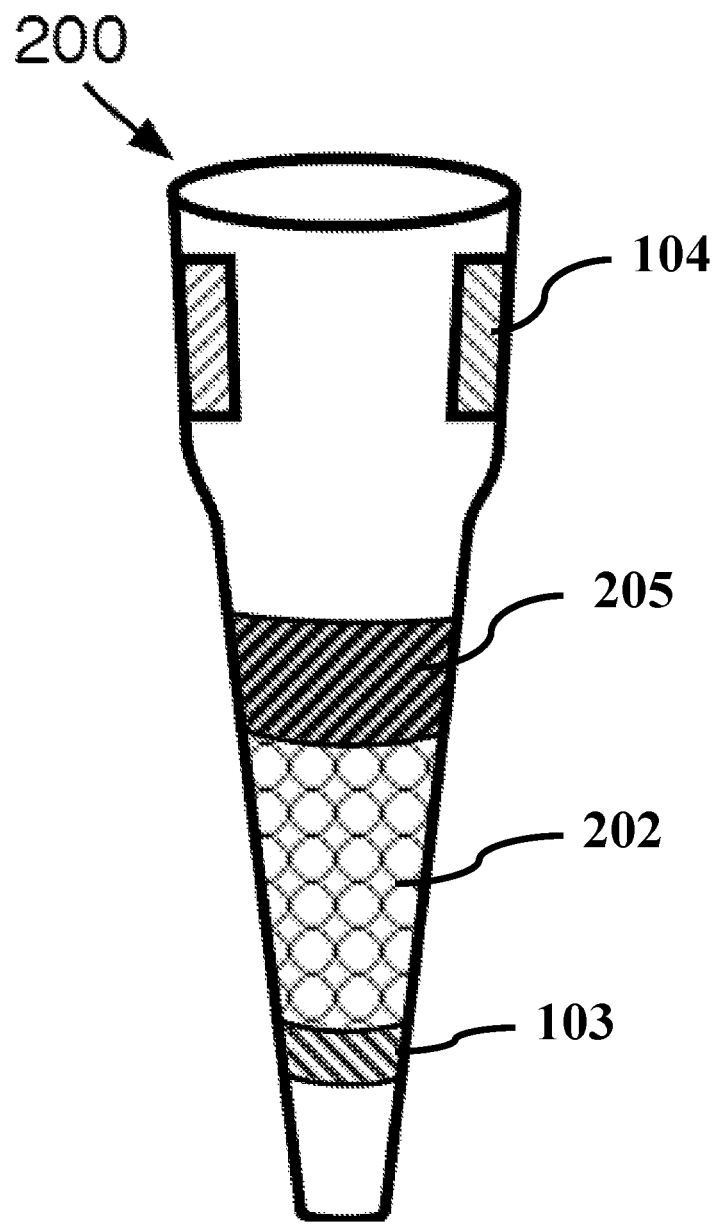
FIG. 2A. One embodiment of the bottom filter pipette tip comprising sorbent and barrier.
Figure 2B:
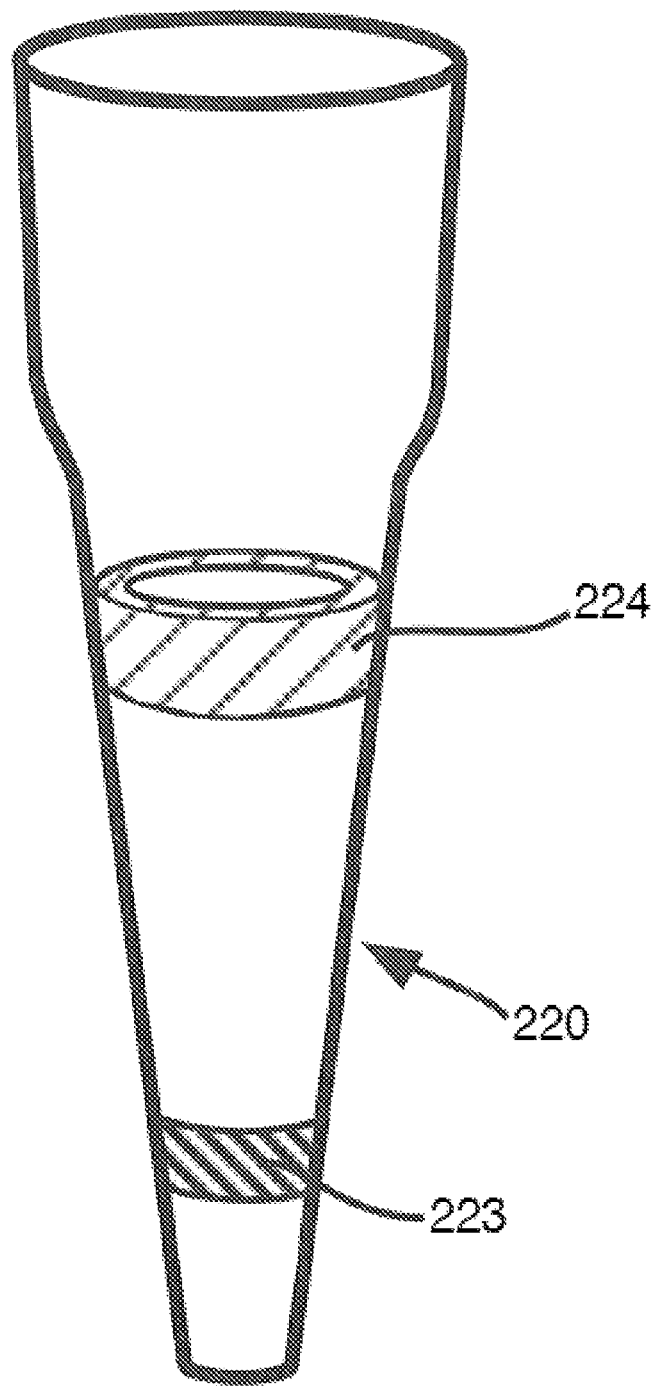
FIG. 2B. Another embodiment of the bottom filter pipette tip with a gasket placed below the hub.

The bottom pipette tip can also include optional sorbents and additional frits or screens to allow for solid phase extraction or precipitation in the tip-on-tip device. FIG. 2A displays a bottom pipette tip having the bottom frit 103, an optional sorbent 202, an optional barrier 205 above the sorbent to keep it contained and not able to contact the top pipette tip 101 and the optional gasket 104. This design allows the bottom pipette tip to participate in extraction or precipitation and still filter the solid sorbent from the solution. FIG. 2B displays another variation of the bottom pipette tip 220 having a filter 223 and a gasket 224 below the hub. This placement would still allow the robotic liquid handler to access the filter pipette tips without problem.

Figure 3:
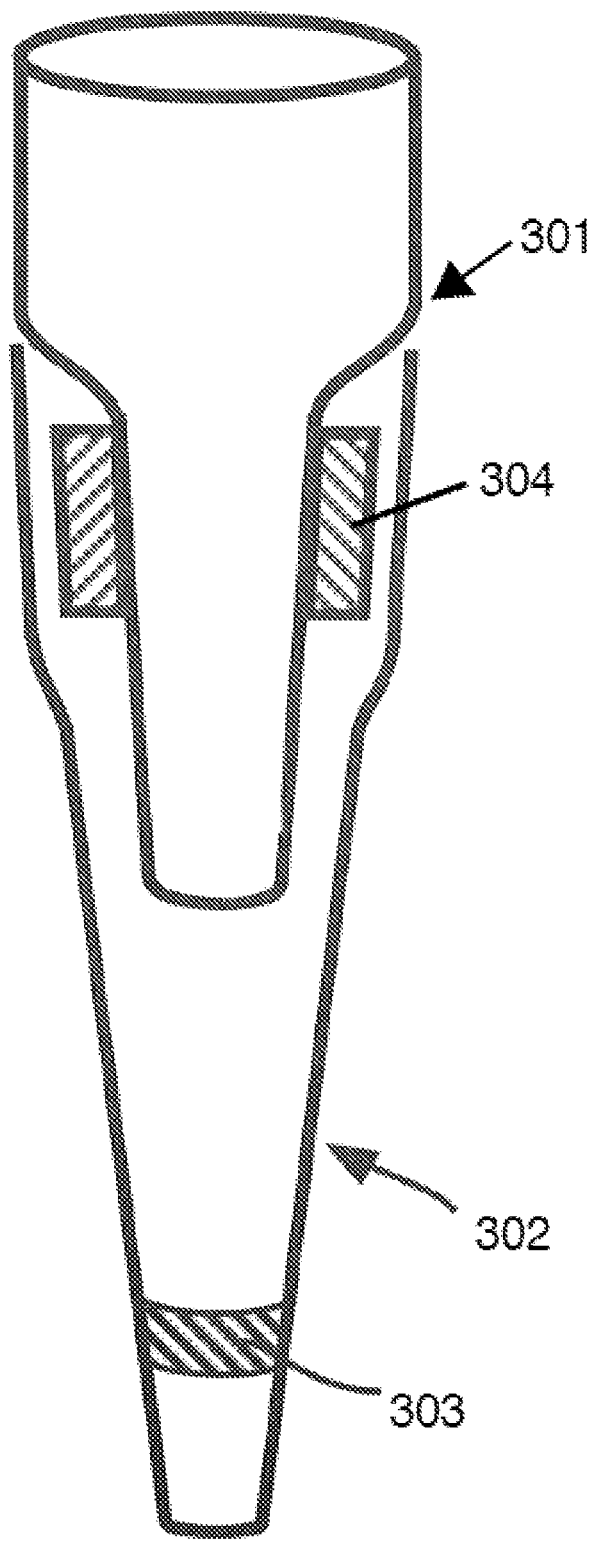
FIG. 3. Expanded tip-on-tip device showing the optional gasket on the top pipette tip. The tips are not shown to scale.

Alternatively, the gasket 304 could be located on the top pipette tip 301 as shown in FIG. 3. Such placement would need to be high enough on the top pipette tip 301 to avoid contact with the filter 303, samples, solvents, and/or sorbents in the bottom filter pipette tip 302.

The exemplary methods for using the devices can be summarized as follows:

Method 1: Protein precipitation performed separately using 'top' wide bore pipette tip followed by filtration using the tip-on-tip device. The 'bottom' filter pipette tip can have optional substrates, sorbents, barriers, or gaskets.

Method 2: Dispersive SPE performed using the top pipette tip followed by filtration with the tip-on-tip device. The top pipette tip is used to transfer sample solution that contains solid particulate matter. The solid particulate matter may be inherent to the sample, or from a dispersive sorbent SPE step performed in the top pipette tip, or may be created due to protein precipitation and/or other treatment of the sample solution. The bottom filter pipette tip filters the solid particulate matter such that a 'clean' liquid passes through. Additional steps such as wash and elution can be performed on the particulate in the tip-on-tip device. This method encompasses 'cleanup' solid phase extraction or the traditional bind-wash-elute process.

Method 3: The precipitation or binding of target compounds to a substrate is performed using the tip-on-tip device. The 'bottom' filter pipette tip must have a substrate or sorbent and/or optional barriers. In this method, the protein precipitation is occurring using the substrate or sorbent of the filter tip to facilitate the precipitation and improve its efficiency. The top tip aspirates the sample, such as serum or plasma, then moves into the filter tip, the sample is delivered to the substrate or sorbent using the tip-on-tip device, and then precipitation solvent is aspirated into the tip-on-tip device and mixed to precipitate the proteins.

In any of the above methods, the tip-on-tip device can utilize a gasket between the pipette tips to facilitate an air-tight seal and optionally a reversible seating between the tips. The gasket alleviates the amount of forces required from the RLH for both forming the tip-on-tip configuration, and optionally removing the top pipette tip if needed.

These methods are exemplified with respect to the following examples. However, these are exemplary only, and the methods can be broadly applied to any biological matrix from any animal or human that contains proteins that interfere with analytes or chemical matrices found in food, environmental or pharmaceutical arts. The following examples are intended to be illustrative only, and not unduly limit the scope of the appended claims.

Method 1

The first tip-on-tip method uses the 'top' pipette tip to repeatedly aspirate the biological sample and precipitation reagent to form the protein precipitate. The supernatant is then aspirated a final time into the top pipette tip, with little to no precipitate, and the RLH moves the top pipette tip to a 'bottom' pipette tip modified with at least a filter, and makes an air tight seal. The supernatant is then pushed through both pipette tips and into a sample well. This filtered sample can then undergo more sample processing and/or analysis.

In more detail, a wide bore pipette tip attached to a robotic liquid handler (RLH) is used to dispense a precipitation reagent into a well containing a biological sample. A precipitation reagent is added to a biological sample to precipitate proteins that interfere with target analytes in the sample. Organic solvents and solutes such as acids, base, acetone, alcohol, urea, guanidine salts, amides, salicylates, ionic detergents, inorganic electrolytes and proteolytic enzymes are commonly used as precipitation reagent to precipitate proteins.

Typically, the interfering proteins may settle by gravity, and mechanical separation techniques are usually employed to speed up the process and obtain a supernatant substantially free of interfering proteins, but containing the target analytes. Thus, the sample and solvent are vortexed and centrifuged by the user-technician to obtain a clear supernatant. These can be time consuming steps that are typically performed by a technician and not the RLH.

The present device allows for the precipitation reagent and sample to be mixed by repeatedly aspirating and dispensing through the wide bore pipette tip, which ultimately precipitates the biological sample's proteins. This reduces time and complexity of the method.

Once precipitated, the solution (i.e. supernatant), with some precipitate, is aspirated into the wide bore pipette tip and carried to a separate tray on the RLH containing filter pipette tips in a well or vial. The filter pipette tip is a standard or robotic pipette tip fitted with a frit or screen and, optionally, a substrate, sorbent, or barrier. The wide bore pipette tip fits within the filter pipette tip to form an air-tight seal and create a tip-on-tip format. Some RLHs may not be able to exert enough force to seal the tip-on-tip device. Thus, some embodiments include filter pipette tips that are fitted with a gasket, such as a square o-ring, that allows the two tips to be seated to form an air-tight seal and alleviates the force needed from the RLH, or use of a gasket on the top mixing pipette tip. This allows the tip-on-tip device to be created and used by RLHs from any manufacturer.

Once the air-tight seal is established, the solution is then dispensed from the wide bore tip through the filter pipette tip, and optional substrate, which cleans and filters the solution. The clean sample solution can then undergo SPE and/or direct analysis by downstream analytical methods.

The entire precipitation process and sample analysis is thus automated by the RLH. This procedure replaces the complexities of vortex mixing and centrifugation with automation and removes the human element. Further, the entire process is much less time consuming than the vortex mixing and centrifugation, allowing for greater sample throughput. Additionally, by not utilizing centrifugation, vacuum or positive pressure manifolds during the filtration process, basic and less expensive robotic systems can be used with the methods.

The 'bottom' filter pipette tip can contain an optional substrate, positioned above the filter, that has minimal active sites so that the precipitant and possible unwanted matrix compounds can stick to the substrate, but target analytes do not.

The substrate may also be a sorbent that targets biological sample matrix components, or may be the same type of sorbent as that used in the HPLC column phase. In some embodiments, a combination of sorbents is utilized to bind a combination of matrix components, but not analytes of interest.

During the protein precipitation process of mixing the precipitation reagent with the sample using the wide bore pipette tip, some precipitate is expected to be carried over into the filter pipette tip from the wide bore tip. However, much of the precipitate remains in the original well. Ideally, the original sample well is wide with high surface area to retain most of the precipitated proteins.

In other embodiments, however, the robotic liquid handler (RLH) can be used to lower and press the top pipette tip into the bottom filter pipette tip, creating an air-tight friction fit seal. This would allow movement of the "tip-on-tip" as one device between sample wells and/or waste containers. This prevents the RLH from having to move the top and filter tips separately, which decreases the time for sample processing.

Any biological sample can undergo protein precipitation using this method, including human and animal samples.

Once the protein precipitate has been removed using the filter pipette tip, the cleaned sample can undergo analysis or further sample preparation. For instance, automated SPE methods such as DPX can be used to extract out certain target molecules such as drugs, or be used to remove matrix components. Thus, the protein precipitation, extraction and analysis are all automated to decrease analysis time, increase throughput, and limit human intervention.

Method 2

Method 2 differs from Method 1 in that a sorbent is added to the sample vial, tube or well containing the sample solution, and mixed therewith thoroughly. The sorbent is selected to remove targeted component(s) of the sample, which can be analytes or matrix components. Then, the tip-on-tip filtration is performed to separate the sorbent from the solution. In some embodiments, a "clean" solution is collected for subsequent analysis because the sorbent removed unwanted matrix. In other embodiments, the collected sorbent undergoes additional steps to remove its bound analytes.

The benefit of this method is a more efficient and potentially longer interaction time can take place between the sample and sorbent than seen in Method 1 (for optional use of SPE). This allows the targeted compounds to partition and bind to the sorbent at a higher rate.

In performing this method, a 'top' pipette tip attached to a robotic liquid handler (RLH) is used to dispense a chemical or biological sample in a well or sample vial containing a sorbent. The sorbent and sample are then mixed by repeatedly aspirating and dispensing through the top pipette tip, which ultimately loads the analyte(s) of interest onto the sorbent. This is essentially a dispersive solid phase extraction wherein the sorbent is not contained.

Once the sorbent is loaded, the solution and sorbent is aspirated into the top pipette tip and carried to a separate tray on the RLH containing the filter pipette tips in a well or vial. The filter pipette tip is a standard or robotic pipette tip fitted with a frit or screen, but no sorbent. The top pipette tip fits within the filter pipette tip to form an air-tight seal and create a tip-on-tip format. Again, a gasket can be used to alleviate the amount of force needed by the RLH to form the tip-on-tip device.

After the air-tight seal is established, the solution is then dispensed from the top pipette tip through the filter pipette tip, which retains the analyte-loaded sorbent.

Depending on the targeted analyte, the tip-on-tip device may be used to aspirate wash solvent such as water in and out of the collected sorbent, and can subsequently aspirate and dispense elution solvent in order to collect the analyte for analysis. The clean solution containing the analyte can then undergo additional sample preparation techniques and/or direct analysis by downstream analytical methods. This is commonly known as a bind-wash-elute procedure. In other embodiments, the targeted compounds can be the matrix itself. Thus, the sorbent collected by the filter pipette tip can be disposed of without additional steps. Each of these examples is described in more detail below.

Matrix Removal:

For matrix removal, the sorbent is selected to remove sample matrix components, and the tip-on-tip filtration is performed to separate out the "clean" solution for subsequent analysis. The sorbent retained in the filter pipette tip is then discarded.

For instance, an immunoaffinity resin sorbent can be used in the sample to bind and remove high concentration proteins in serum or plasma. Immunoaffinity resins bind the protein by thoroughly mixing with the sample solution. In most sample preparation procedures, this mixing can occur by placing the sample tube, containing the e.g. serum sample and sorbent, onto a mixer which may be temperature controlled. However, it may be practical to simply use the top wide bore pipette tip to thoroughly mix the immunoaffinity resin with the sample solution by repeatedly aspirating and dispensing the solution in and out of the top pipette tip. After sufficient binding of the protein to the immunoaffinity resin, the top pipette tip can subsequently aspirate the solution and be seated into the filter pipette tip, allowing transfer of the solution through the filter pipette tip into a sample vial. The collected solution would then be free of the high concentration of protein.

If the immunoaffinity resin sorbent has a much greater density than the sample solution, the top pipette tip would need to transfer as much of the supernatant as possible, leaving much of the sorbent in the tube. However, if the immunoaffinity resin sorbent is dispersed and does not settle readily, the top pipette tip could potentially transfer all of the sorbent to the filter pipette tip to separate the solution from the unwanted protein and immunoaffinity resin.

An additional example of this variation involves the field of food safety. Though not directed to protein precipitation, this method can be used to remove water and fatty acids in food samples using the QuEChERS products. The QuEChERS products contain set amounts of $MgSO_4$ and primary secondary amine (PSA) to remove water and fatty acids, respectively, and may optionally contain C18 and/or graphitized carbon black (GCB) to remove nonpolar compounds and chlorophyll, respectively. It has been shown that dispersive solid phase extraction in QuEChERS methods is much preferred over packed QuEChERS cartridges. Higher recoveries of pesticides from fruit and vegetables are obtained through dispersive QuEChERS, but these methods are not readily coupled to automation due to the need for centrifugation.

Although QuEChERS tips have been developed, the use of the tip-on-tip method permits highly efficient mixing of the QuEChERS sorbent with the sample solution. After mixing the QuEChERS sorbent with the sample by repeated aspirations with the top pipette tip, the top pipette tip can collect the supernatant and then transfers the solution through the filter pipette tip, as described above, to collect a sample solution free of water and fatty acids (and possibly chlorophyll or lipids).

Use of this tip-on-tip method is particularly advantageous because the use of centrifugation may still lead to particulate matter being transferred in conventional dispersive QuEChERS. This is not a concern with the Tip-On-Tip Method because the solution is filtered.

"Bind-Wash-Elute"

For a "bind-wash-elution" process, the sorbent targets the analytes. After the bottom filtration pipette tip collects the sorbent, additional wash and elution solvents can be aspirated and mixed with the sorbent to remove the analytes from the sorbent from the tip-on-tip device.

This particular method reduces the need to use filter plates and their associated positive or negative pressure manifolds.

An example of the bind-wash-elution method is the use of immunoaffinity sorbent to bind specific peptides or drugs. The binding is performed by mixing the sorbent in a tube at a specific controlled temperature for a couple hours to obtain high recovery. This dispersive SPE cannot be readily performed in a pipette tip or cartridge due to the temperature control and extended time for mixing. After this incubation period, the wide bore tip aspirates the slurry of the immunoaffinity sorbent and transfers the solution through the filter pipette tip. After collecting the sorbent, the tip-on-tip device can move to a wash well plate and aspirate and dispense wash solution to waste. Afterwards, the tip-on-tip device can move to the well plate with elution solvent to aspirate and dispense the solvent to elute the analyte of interest for subsequent analysis.

In some embodiments, it may be advantageous to wash and elute the analyte from the sorbent by adding solvents to the top of the sorbent ("top-down") contained in the filter pipette tip. In that case, the top pipette tip would have to be reversibility fitted to the filter pipette tip so that it can be removed to allow for another pipette tip or top pipette tip to dispense solvents to the top of the sorbent in the filter pipette tip. In such situations, the filter pipette tip has to have the gasket so it does not irreversibly seal, like a hard o-ring that tends to push the top pipette tip out; in this case, the filter pipette tip would have to be mounted on a stand so that the top pipette tip is pushed against the filter tip to provide a seal. Alternatively, the gasket could be mounted on a top pipette tip to provide positive pressure to the filter tip. However, care must be taken so that the gasket is positioned to not come in contact with solvents, sorbents or other solutions that the top pipette tip has to gather. In addition to alleviating the amount of force required by the RLH to seat the tips, this type of gasket also allows for easy reversal of the fitting.

Method 3

Method 3 uses sorbent to facilitate the protein precipitation. In this case, the sample is added to the sorbent first, and then precipitation solvent is mixed with the sorbent inside the filter pipette tip.

Method 3 utilizes a 'bottom' filter pipette tip and has a substrate sorbent (i.e. it is no longer optional), and the precipitation or extraction or cleaning steps take place in the bottom filter pipette tip. In Methods 1 and 2, the mixing took place in the top pipette tip.

In more detail, the top pipette tip aspirates the untreated biological or chemical sample. The RLH then moves this tip and sample to the second, bottom filter pipette tip. The top pipette tip is pressure fitted to the bottom tip using the RLH to form a single piece tip-on-tip device. The two pipettes tips are fitted such that the RLH will be able to aspirate and dispense solvent though the tip-on-tip device. Again, a gasket placed in the wide end of the filter pipette tip can be used to alleviate the amount of force needed by the RLH to seat the top pipette tip.

Once in place, the biological or chemical sample is eluted from the top pipette tip onto the sorbent in the bottom pipette tip. Reagents (e.g. precipitation reagents) can then be aspirated from the bottom pipette tip into the sorbent and mixed with the sample therein. Thus, in the case of precipitation reagents, the protein precipitation occurs in the presence of the substrate. As with Method 1, the precipitation reagent can be repeatedly aspirated and dispensed to form the protein precipitate. However, the protein precipitate remains inside the bottom pipette tip with the sorbent. The final precipitation reagent elution can undergo further clean up before analysis if necessary.

The bottom pipette tip can be located in a sample well containing the precipitation reagent when the top pipette tip is fitted to it. Or, alternatively, the bottom pipette tip can be located in a pipette tip tray, the top pipette tip can be pressured into the bottom tip, and then the RLH can move the single piece tip-on-tip device to a sample well containing the precipitation solvent or reagent.

This method uses the same pipette tips, sorbents, filters, and the like as Method 1 and Method 2. The only difference is the requirement for substrate in the bottom pipette tip, which was optional in Method 1, and the change in the sequence of the formation of the tip-on-tip device with respect to the protein precipitation step.

By using the substrate during the protein precipitation, improved recoveries were observed for Method 3 than with the traditional vortex mixing and centrifugation based methods. We believe the sorbent acts as a solid support for the protein precipitation process, which helps to increase the interaction of the solvent with analyte by providing a high surface area medium to contain the protein.

Vitamin D

A comparison of the traditional protein precipitation method and the currently disclosed automated Method 1 were performed for the analysis of 25-hydroxy vitamin $D_3$ in human serum.

For both methods, each sample contained 100 μL of serum mixed with 300 μL acetonitrile as the precipitation reagent.

For the traditional protein precipitation, the samples and solvents were vortexed for 2 minutes and centrifuged for 10 minutes to separate the precipitate and supernatant. The supernatant was then removed with a hand-held pipettor and placed in sample vials. The analytes in the supernatant were subsequently extracted using a solid-phase extraction method using dispersive pipette extraction (DPX) before analysis by liquid chromatography/mass spectrometry/mass spectrometry (LC/MS/MS). The DPX devices are described in U.S. Pat. No. 6,566,145, which is incorporated herein for all purposes.

For the automated Method 1, the 100 μL serum aliquot was placed in its own well. Then, 300 μL of acetonitrile was dispensed into each sample well simultaneously, via the robotic liquid handler, through wide bore pipette tips into the sample wells. The sample and solvent were then aspirated and dispensed three times in a controlled manner. This allowed for the solvent to quickly and efficiently precipitate the protein. The aspiration and dispensing steps provided rigorous mixing of the solutions, causing rapid precipitation of the sample.

Further, more and more precipitated protein clung to the sample well after each dispensing step, allowing the protein and supernatant to mostly separate. On the final aspiration step, the wide bore tip was positioned slightly raised so that the aspirated solution was predominantly supernatant with a small amount of solid precipitated protein. The RLH then moved the wide bore tip containing the supernatant to a pipette tip tray having the bottom, filter pipette tips.

In this example, the filter pipette tip was a pipette tip modified to have two porous frits, one larger frit that is more porous and a smaller frit at the narrow end of the pipette tip. No additional substrate or barrier was utilized. The wide bore tip was lowered and pressed into the filter tip using the RLH, creating an air-tight friction fit seal. The "tip-on-tip" with sample solution was then moved to a second well plate.

The sample supernatant in the 'top' wide bore pipette tip was eluted through the attached filter pipette tip and into the second well plate. The RLH was able to discard the wide bore pipette tip and attached filter pipette tip into the waste bin. The entire automated protein precipitation and filtration took less than 3 minutes to perform without any additional accessories on the robotic handler. Moreover, this fast process was performed to include up to 96 samples simultaneously.

These samples were subsequently extracted using the same solid-phase extraction method as the above and analyzed by LC/MS/MS.

Figure 4:
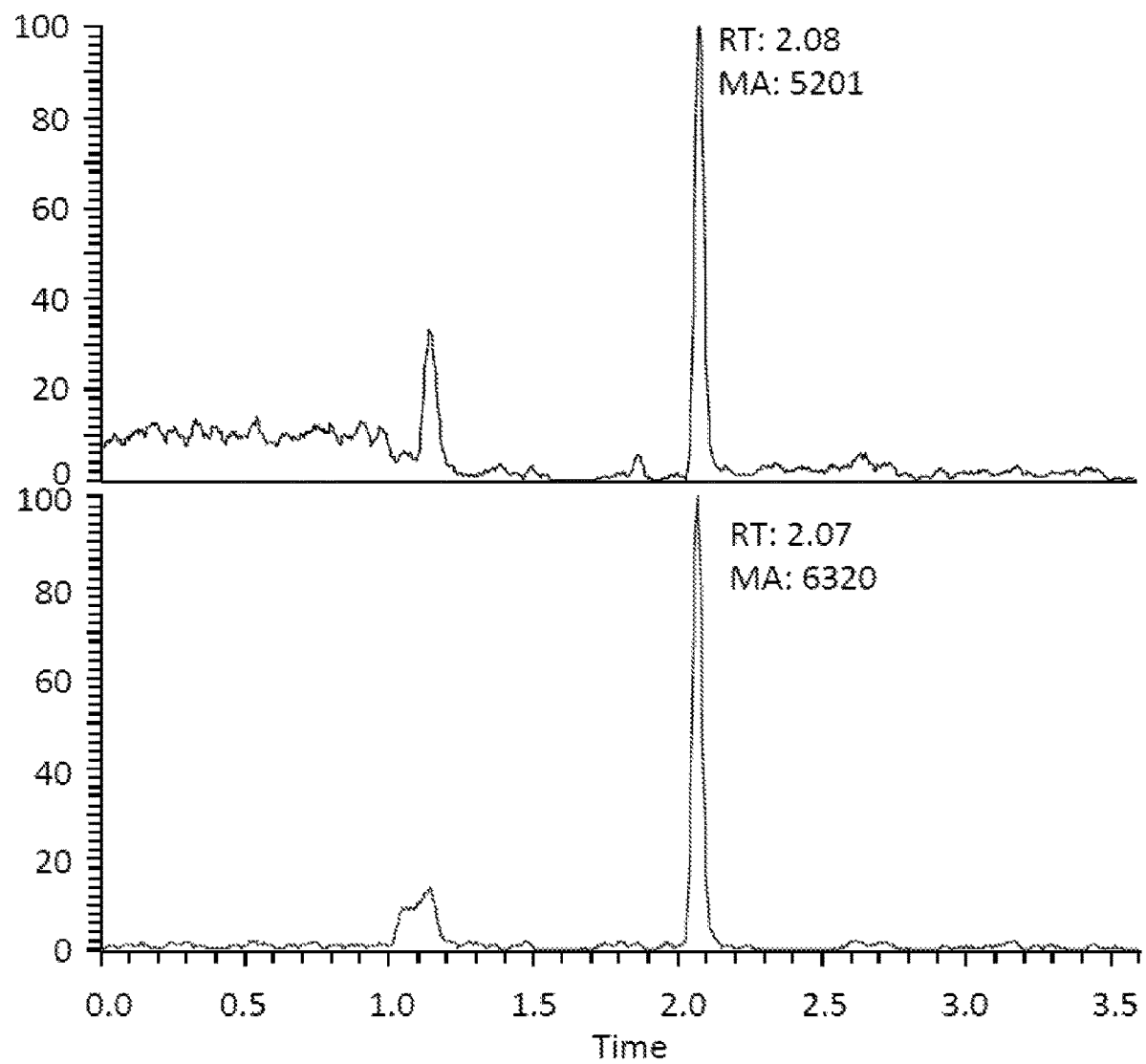
FIG. 4. Chromatogram of Vitamin D extraction using a traditional centrifugation method (top) and the disclosed filtration method (bottom).

The chromatograms are shown in FIG. 4, with the results from the traditional centrifugation-based method in the top chromatograms and the results from the disclosed automated tip-on-tip filter method on the bottom. Detailed studies showed no statistically significant difference in the quantitative results obtained between the 2 methods, as shown in Table 1. However, the time needed to perform the protein precipitation decreased five-fold with the presently disclosed method.

TABLE 1

Comparison of Automated Method 1 using tip-on-tip device and traditional Centrifuged precipitation

| Patient Sample | Automated Filter Method Conc. (ng/mL) | Centrifugation Method Conc. (ng/mL) | % Difference* |
|---|---|---|---|
| 1 | 15.4 | 16.1 | −4.4 |
| 2 | 29.5 | 30.7 | −3.9 |
| 3 | 48.0 | 43.6 | 10.1 |
| 4 | 26.0 | 24.5 | 6.1 |

*% Difference = (Auto-Cent)/(Cent) × 100%

The automated filter method using the "tip-on-tip" format was able to recover as much as, if not more, of the target analyte from real patient samples. This shows that the currently disclosed automated method is as good as the traditional methods for recovering analytes, but much quicker, leading to higher throughput.

Hormones

The method delineated above for 25-hydroxy vitamin $D_3$ was also repeated for analysis of total testosterone in serum. The serum sample was a commercial quality control sample. The precipitation and analysis was repeated with four samples. The results of the automated Method 1 sample preparation combined with an automated DPX extraction are shown in Table 2.

Figure 5:
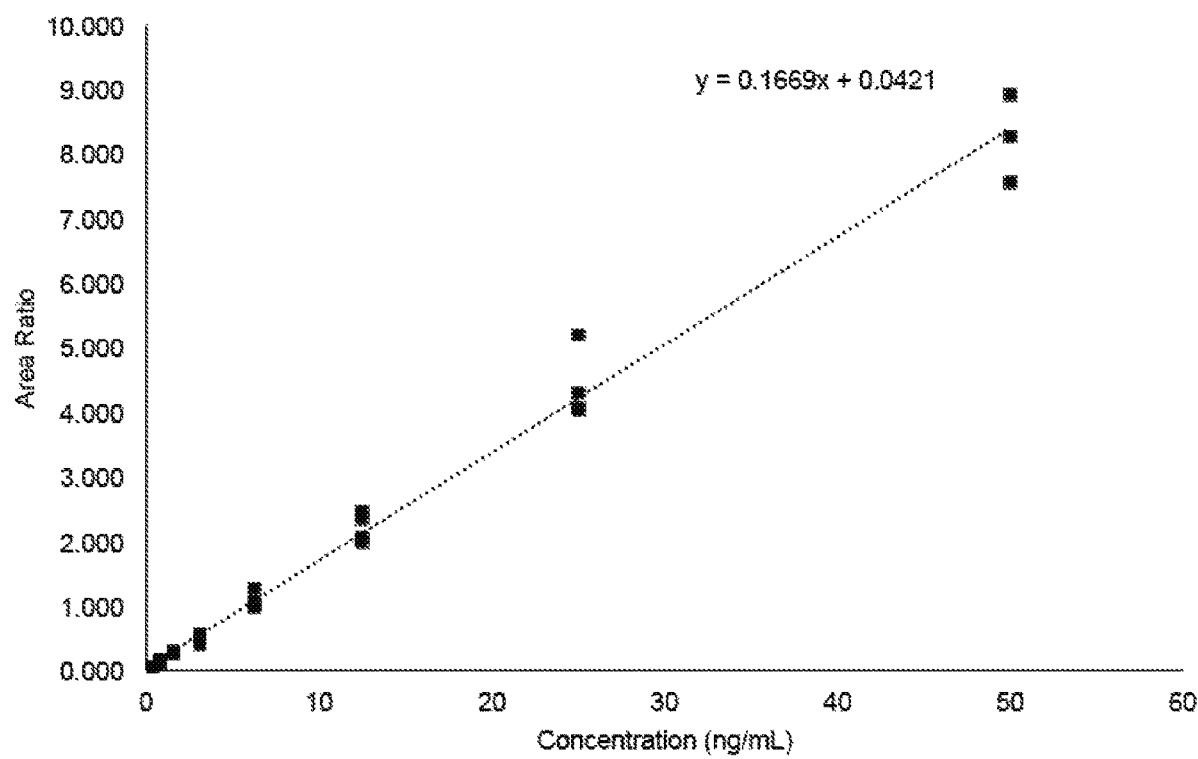
FIG. 5. Calibration plot of total testosterone analyzed by the automated tip-on-tip method followed by DPX extraction.

FIG. 5 shows a calibration plot of total testosterone analyzed by the automated tip-on-tip Method 1 precipitation followed by DPX extraction. This plot shows that the tip-on-tip method is applicable to a wide range of analyte concentrations.

TABLE 2

Results for total testosterone from a commercial quality control serum samples using Method 1, tip-on-tip format.

| Sample | Calculated concentration (ng/mL) | Concentration (ng/mL) | Accuracy (%) |
|---|---|---|---|
| Control 1 | 0.9 | 0.859 | 95.4 |
| Control 2 | 1.82 | 1.79 | 99.2 |
| Control 3 | 4.55 | 4.16 | 91.4 |
| Control 4 | 9.1 | 9.38 | 103 |

Drugs of Abuse

In addition to hormones and vitamins, biological samples containing drugs of abuse were also analyzed. The automated Method 1, delineated above for 25-hydroxy vitamin $D_3$, was also repeated for analysis of drugs of abuse in whole blood, although smaller sample sizes were used.

A whole blood sample was spiked at 25 ng/mL of a drug mixture (listed in Table 3). The traditional precipitation method was performed by vortex mixing 50 μL whole blood with 200 μL of acetonitrile as a precipitation reagent, and then subsequently centrifuging the samples. These samples were then processed using DPX tips for extraction.

The whole blood sample was also processed as described above using the automated precipitation and filtration method with the "tip-on-tip" format using 200 uL acetonitrile. The blood was protein precipitated, filtered, and subsequently extracted using DPX tips with a Hamilton Nimbus96 system. In approximately 3 minutes, up to 96 whole blood samples were extracted and ready for LC/MS analysis. In this study, the results of the completely automated method using the "tip-on-tip" format with DPX extraction were the same as those obtained using vortex mixing and centrifugation with DPX extraction. Overall recoveries were over 50%. Table 3 below shows results from this study.

TABLE 3

Results of tip-on-tip method 1 for extracting drugs from whole blood.

| Compound | % Recovery |
|---|---|
| Morphine | 64 |
| Oxymorphone | 61 |
| Hydromorphone | 72 |
| Codeine | 61 |
| Pregabalin | 66 |
| Gabapentin | 97 |
| oxycodone | 62 |
| 6-MAM | 76 |
| Methamphetamine | 71 |
| Hydrocodone | 78 |
| 7-aminoclonazepam | 77 |
| Benzoyl ecgonine | 72 |
| Ritalinic acid | 66 |
| N-desmethyl tramadol | 62 |
| Tramadol | 69 |
| Cocaethylene | 67 |
| Meperidine | 72 |
| Zolpidem | 71 |
| PCP | 72 |
| Fentanyl | 88 |
| Cyclobenzaprine | 72 |
| Amitriptyline | 83 |
| alpha-hydroxyalprazolam | 78 |
| Methadone | 66 |
| Oxazepam | 66 |

TABLE 3-continued

Results of tip-on-tip method 1 for extracting drugs from whole blood.

| Compound | % Recovery |
| --- | --- |
| Lorazepam | 66 |
| Alprazolam | 77 |
| Nordiazepam | 62 |
| Temazepam | 70 |
| Diazepam | 69 |

This method took less than 3 minutes to process up to 96 samples simultaneously using a 96 head RLH. The results below show that this method is ideal for comprehensive screening of drugs in whole blood.

Drug Delivery Systems

Method 2 can be used as a conventional filtration step using the tip-on-tip configuration, or for SPE. The solid particulate matter may be inherent to the sample, or from a dispersive sorbent SPE step performed in the top pipette tip or may be created due to protein precipitation (Method 1) and/or other treatment of said sample solution. The use of the pipette tips for filtration simplifies the liquid handling program for the robotics and reduces the amount of extra accessories needed on the RLH platform.

An example of the types of sample processing that can benefit from this method is the analysis of active pharmaceutical ingredients (API) in various drug delivery systems including tablets, pills and capsules. As an example, a crushed tablet can be mixed with organic solvent. Much of the excipients may not dissolve in the solvent, but the API is readily soluble. By aspirating and dispensing the solution, the sample is readily mixed. The particulate matter, which may be composed of inert ingredients, is filtered and removed by using the tip-on-tip method, thereby collecting the sample solution for analysis.

The analysis of some drugs can be difficult due to the presence of the matrix. For example, analysis of the API in gelatin material involves the tedious step of removing the gelatin protein. To mimic such an analysis, candy composed of gelatin (e.g. gummy bears) was prepared for analysis and Method 2 was utilized to filter the solid components of the drying agent used for precipitation.

The gummy bears were dissolved in water using heat and a shaker for approximately 30 min at 50° C. This aqueous solution was then diluted 3:1 in acetonitrile (300 μL of acetonitrile added to 100 μL of the aqueous solution of gummy bears) to form the sample solution. The sample solution was cloudy from the gelatinous precipitation, suggesting the protein was not completely precipitated or dissolved.

An aliquot of the sample solution was subsequently delivered to a test tube containing 300 mg of anhydrous $MgSO_4$. The sample solution and $MgSO_4$ was mixed by aspirating and dispensing the solution 4-5 times using a wide bore top pipette tip. The top pipette tip was subsequently used to aspirate the solution, containing some $MgSO_4$ particulate matter, and was seated into the filter pipette tip with a square o-ring as a gasket.

Once the tip-on-tip configuration was formed, the solution was passed through the filter of the filter pipette tip into a vial. The resulting dispensed solution was clear and free from protein precipitation. The anhydrous $MgSO_4$ was used to remove the water from the acetonitrile extract, which resulted in the complete precipitation of the gelatin protein.

This method (after dissolving the sample) took less than one minute to perform, and the clean acetonitrile solution was ready for analysis of the API. For higher recoveries if needed, a second aliquot of acetonitrile could be added to the tube containing the used $MgSO_4$ to collect any residual API, with subsequent filtration using tip-on-tip.

Cleanup SPE

In addition to simple filtration, Method 2 also allows for a 'cleanup' solid phase extraction using the top pipette tip as a pre-filtration step. Here, the sample solution was first mixed with sorbent using the top pipette tip, similar to the protein precipitation in the previous examples. The sorbent bound and removed sample matrix components from the solution. The filter pipette tip was subsequently used to collect the sorbent and allowed the analyte-rich solution to pass through for further analysis.

An example of the types of sample processing that can benefit from this method is the QuEChERS process. The method of QuEChERS involves the use of anhydrous $MgSO_4$ and PSA to remove water and fatty acids from acetonitrile extracts of food. There are many variations of QuEChERS methods, and some include the removal of chlorophyll using graphitized carbon black added to the $MgSO_4$ and PSA.

Many QuEChERS solid phase extraction devices exist. It has been reported in the literature that dispersive QuEChERS, using freely moving sorbent, is more efficient than using cartridges with packed sorbent. However, the dispersive QuEChERS devices still require shaking and centrifugation, which are not often readily automated steps.

The QuEChERS cleanup process was performed using dispersive extraction with the tip-on-tip devices. In this example, 1 mL of acetonitrile extract from an orange concentrate was prepared using a QuEChERS preparation packet. The acetonitrile extract was placed into a test tube containing 150 mg of $MgSO_4$ and 75 mg of PSA. The solution, $MgSO_4$ and PSA were mixed by repeatedly aspirating and dispensing with the wide bore top pipette tip. The solution containing primarily supernatant, after allowing the sorbent to settle, was aspirated a final time by the top pipette tip before being moved to the filter pipette tip. Once an air-tight seal was formed between the seated tips, the solution was dispensed through filter pipette tip and collected for analysis. The solid particulates from the supernatant remained in the filter pipette tip. Table 4 shows recoveries and reproducibility (as percent relative standard deviation (% RSD)) from this study.

This tip-on-tip QuEChERS cleanup method provides two primary advantages then the conventional method of using centrifugation: 1) The method can be readily automated without a centrifuge; and 2) the final solution is essentially guaranteed to be particulate free. If using centrifugation, it is possible that residual sorbent can be transferred from the centrifuge tube to the vial for analysis, causing the injection system of the analytical instrument to become clogged.

TABLE 4

Recoveries and % RSDs using the dispersive QuEChERS and tip-on-tip filtration of pesticides spiked in orange concentrate.

| Pesticide | % Recovery | % RSD |
|---|---|---|
| DPA | 90.3 | 4.09 |
| Atrazine | 89.9 | 4.45 |
| Methyl parathion | 87.8 | 2.91 |
| Malathion | 90.5 | 1.54 |
| Chlorpyrifos | 91.4 | 4.08 |
| Cyprodinil | 92.5 | 2.94 |
| Bioallethrin | 89.9 | 2.57 |
| Fludioxonil | 92.0 | 2.97 |
| Bifenthrin | 93.1 | 6.04 |
| Boscalid | 92.1 | 5.80 |

Precipitation

In addition to the automated Method 1, Method 3 can achieve similar recoveries by performing the protein precipitation in the bottom filter pipette tip.

Method 3 differs from Method 1 in a couple of ways. First, the bottom filter pipette tip must contain a sorbent. In Method 1, the sorbent was an optional feature. In addition to the mandatory sorbent, the bottom filter pipette tip can also contain substrates, barriers and combinations thereof.

Second, the protein precipitation takes place in the filter pipette tip device. In Method 1, the precipitation occurs in a sample vial using the top, wide bore tip, and the supernatant was then eluted through the tip-on-tip device.

In Method 3, the sample is added to the top of the sorbent once the two pipette tips are fitted together and the precipitation reagent is aspirated through the sorbent (from the bottom filter tip).

In the current test, whole blood was spiked with a collection of common drugs of abuse and their metabolites. The list of drugs and the results of the analysis is shown in Table 5. The precipitation reagent was acetonitrile.

The steps for the traditional centrifugation method were described above for Drugs of Abuse. After centrifugation and filtration, the supernatant was cleaned with DPX tips containing a weak anion exchange (WAX) sorbent.

For the automated Method 3, the precipitation steps are as follows:

The 'top' pipette tip aspirated the whole sample blood.
The RLH moves the 'top' pipette tip to a tray containing the 'bottom' filter pipette tip and presses the top pipette therein. The filter tip contained a weak anion exchange (WAX) sorbent.
The tip-on-tip device is then moved to a sample vial containing the precipitation reagent, acetonitrile, using the RLH.
RLH dispensed the blood from the 'top' pipette tip into the bottom filter pipette tip and on top of the WAX sorbent.
The acetonitrile was aspirated from the bottom of the filter pipette tip to crash (i.e. precipitate) the proteins in the presence of the WAX sorbent. The acetonitrile was then dispensed. The acetonitrile was aspirated and dispensed a second time.
The dispensed acetonitrile was solvent evaporated and reconstituted in 10% methanol before being analyzed.
Samples prepared by both methods were then analyzed using LC/MS/MS.

By performing the protein precipitation in the presence of the sorbent, we unexpectedly found reduced ion suppression and better recoveries with the automated Method 3 than traditional centrifugation methods. As shown in Table 5, the ion suppression significantly decreased for most of the analytes while the recoveries improved.

TABLE 5

Comparison of Automated Method 2 and Centrifuged precipitation using WAX cleanup

| Drugs of Abuse | Crash/Centrifuge with WAX Clean-Up | | PPT WAX + Acid Acetonitrile | |
|---|---|---|---|---|
| | Ion Suppression | Recovery | Ion Suppression | Recovery |
| Morphine | 24 | 44 | 3 | 85 |
| Oxymorphone | 36 | 45 | 9 | 86 |
| Hydromorphone | 32 | 46 | 8 | 87 |
| Gabapentin | 45 | 31 | 18 | 59 |
| Codeine | 50 | 51 | 40 | 114 |
| Pregabalin | 46 | 25 | 1 | 60 |
| Oxycodone | 57 | 62 | 31 | 106 |
| 6-MAM | 31 | 39 | 26 | 58 |
| Hydrocodone | 44 | 62 | 29 | 96 |
| Methamphetamine | 91 | 74 | 5 | 65 |
| MDEA | 73 | 68 | 3 | 89 |
| Benzoylecognine | 59 | 87 | 41 | 149 |
| Norfentanyl | 10 | 62 | 14 | 102 |
| N-Desmethyltramadol | 22 | 72 | 29 | 104 |
| Tramadol | 67 | 75 | −1 | 81 |
| Cocaethylene | 14 | 46 | −2 | 56 |
| Meperidine | 88 | 70 | 19 | 80 |
| Zolpidem | 1 | 60 | 20 | 87 |
| Norbuprenorphine | −15 | 52 | −3 | 72 |
| Fentanyl | 5 | 65 | 4 | 78 |
| Buprenorphine | 16 | 44 | 50 | 95 |
| Nortriptyline | −40 | 55 | −15 | 67 |
| alpha-hydroxyalprazolam | 7 | 63 | 71 | 101 |
| Amitriptlyine | −14 | 57 | −49 | 75 |
| Oxazepam | 7 | 67 | 49 | 89 |
| Alprazolam | 1 | 74 | 18 | 76 |
| Lorazepam | 12 | 68 | 25 | 74 |
| THC-COOH | 69 | 61 | 92 | 25 |
| THC | 88 | 19 | 86 | 22 |

Micro-SPE Using Tip-on-Tip

The conventional bind-wash-elute in Method 2 with tip-on-tip device was also utilized to extract drugs from serum without performing a protein precipitation step. The goal in this example was to develop a method to extract drugs from a small volume of serum without a protein precipitation step and using a very low elution solvent volume. The results from using a DPX containing 1 mg of reverse phase sorbent (styrene divinyl benzene) for extraction was compared with the tip-on-tip device using a dispersive reverse phase solution in a tube (also containing 1 mg reverse phase sorbent).

For both the tip-on-tip and DPX methods, the extraction was performed on 50 μL serum with only 50 μL of an elution solvent. The serum was spiked at 20 ng/mL of a drug mixture, diluted with 50 μL of 4% $H_3PO_4$, and mixed.

The DPX tips were first conditioned by aspirating and dispensing 100 μL methanol followed by 100 μL of water. The serum sample solution was slowly aspirated into the DPX tip, allowed to mix with the reverse phase sorbent for approximately 20 seconds, and then dispensed. The aspirating/dispensing steps were repeated 4 more times to ensure efficient interaction between the serum sample solution and the sorbent. After extracting the analytes from the serum, the sorbent was washed by aspirating and dispensing 100 μL water in and out of the DPX tip. Subsequently, the analytes were eluted by aspirating and dispensing just 50 μL of methanol for a total of 3 times. The total time for this extraction was approximately 8 min.

For the tip-on-tip SPE method, the 1 mg of sorbent was contained in a sample tube as a slurry (sorbent+10 μL of a 20% methanol solution). 50 μL of each serum sample and acid were added to the sample tube. The resulting solution was mixed by aspirating and dispensing the solution five times using a wide bore tip. After the final mixing step, the solution was aspirated completely into the top wide bore tip, then moved on top and into the bottom filter pipette tip to form the tip-on-tip device. The solution was dispensed, and the sorbent was collected in the bottom filter pipette tip while the fluid passed through. The tip-on-tip device was then moved into a sample tube containing a wash solvent comprising water. The wash solvent was aspirated and dispensed to remove matrix components such as salts. Air was also dispensed through the tips to further remove excess water. Finally, the tip-on-tip device was moved into another sample tube containing 50 μL of methanol as an elution solvent, which was aspirated and dispensed three times to elute the drugs from the sorbent. The total time to complete this tip-on-tip SPE method was under 3 minutes. The elution solvent containing extracted drugs were then analyzed.

Results from the DPX method and the tip-on-tip SPE method are shown in Table 6. Not only did the tip-on-tip SPE method provide higher recoveries of analyte, but the extraction process was much faster.

TABLE 6

Comparison of conventional DPX method with tip-on-tip SPE (bind-wash-elute) using 1 mg of reverse phase sorbent with 50 μL methanol for elution solvent.

|  | DPX | Tip-on-Tip |
| --- | --- | --- |
| Morphine | 10,202 | 14,483 |
| Codeine | 24,946 | 27,934 |
| Gabapentin | 112,142 | 154,968 |
| Methamphetamine | 363,975 | 522,035 |
| Benzoylecgonine | 206,901 | 254,580 |
| Norbuprenorphine | 1,258 | 1,509 |
| Fentanyl | 222,105 | 241,652 |
| Alprazolam | 64,948 | 30,023 |
| Carboxy-THC | 7,520 | 9,309 |

This micro SPE extraction method could be extended to analyze small drugs in biological matrices as well as drugs conjugated to antibodies or contained as nanoparticles. It is possible to analyze the "free drugs" as well as the larger compounds of interest by incorporating steps to analyze them separately. For instance, the free drug could be analyzed by the above tip-on-tip micro SPE method, and then the drug-conjugate or nanoparticle product could be analyzed after protein precipitation or treatment to release the free drug. Alternatively, sorbent could be used for size exclusion, and the analytes of interest detected by incorporating tip-on-tip methods described above.

The following references are incorporated by reference in their entirety for all purposes.

U.S. Pat. No. 6,566,145
U.S. Pat. No. 6,737,023
U.S. Pat. No. 6,171,553

The invention claimed is:

1. A method of automated dispersive solid phase extraction, comprising:
    a) introducing a sample containing at least one target compound into a first sample well on a sample tray on a robotic liquid handler, wherein said first sample well contains a sorbent in a slurry;
    b) mixing said sorbent slurry and said sample by shaking on said robotic liquid handler or by repeatedly aspirating and dispensing with a top pipette tip on said robotic liquid handler to load said at least one target compound onto said sorbent;
    c) waiting a set time period to allow said sorbent slurry to settle;
    d) aspirating to remove a portion of said sample without removing said sorbent slurry;
    e) pipetting a buffer into said first sample well to dilute said sorbent slurry;
    f) repeat steps b) through e) one or more times to remove a remaining portion of said sample;
    g) aspirating said sorbent slurry into said top pipette tip;
    h) moving said top pipette tip with said robotic liquid handler to a pipette tip tray having at least one bottom filter pipette tip;
    i) inserting said top pipette tip into said bottom filter pipette tip to form a tip-on-tip device, wherein said bottom filter pipette tip contains a screen or porous frit at a distal delivery end, wherein said top pipette tip contacts said bottom filter pipette tip to form an airtight seal between said top pipette tip and said bottom filter pipette tip;
    j) dispensing said sorbent slurry from said top pipette tip of said tip-on-tip device through said bottom filter pipette tip and into a second well or waste, wherein said sorbent is retained by said screen or porous frit in said bottom filter pipette tip;
    k) moving said tip-on-tip device as a single piece with said robotic liquid handler to a third well containing a wash solvent;
    l) aspirating said wash solvent into said tip-on-tip device and dispensing said wash solvent into said third well or a waste container;
    m) moving said tip-on-tip device as a single piece with said robotic liquid handler to a fourth well containing an elution solvent; and,
    n) aspirating said elution solvent into said tip-on-tip device and dispensing said elution solvent into said fourth well to form a second solution, such that said elution solvent contacts said sorbent retained by said screen or porous frit, thereby eluting said at least one target compound from said sorbent into said second solution.

2. The method of claim 1, where said target compound is DNA.

3. The method of claim 1, where said target compound is RNA.

4. The method of claim 1, where said target compound is protein.

5. The method of claim 1, where said sample is saliva.

6. The method of claim 1, wherein said sample is selected from a group consisting of serum, plasma, whole blood, urine, spinal fluid, meconium and tissue homogenate.

7. The method of claim 1, where said sample is at least as viscous as human saliva.

8. The method of claim 1, wherein said sorbent is used in an amount with a known capacity for said at least one target compound and said sample contains an amount of said at least one target compound that exceeds said known capacity.

9. The method of claim 1, where said sorbent is selected from a group comprising immunoaffinity resin, polar oligomeric hydrocarbon resin, non-polar oligomeric hydrocarbon resin, weak or strong anion exchange resin, weak or strong cation exchange resin, silica or combinations thereof.

* * * * *